United States Patent [19]

Arnold

[11] 4,165,229

[45] Aug. 21, 1979

[54] HERBICIDAL METHOD

[75] Inventor: Wendell R. Arnold, Delray Beach, Fla.

[73] Assignee: Eli Lilly and Company, Indianapolis, Ind.

[21] Appl. No.: 828,699

[22] Filed: Aug. 29, 1977

Related U.S. Application Data

[63] Continuation-in-part of Ser. No. 683,872, May 6, 1976, abandoned, which is a continuation-in-part of Ser. No. 533,897, Dec. 18, 1974, Pat. No. 3,972,706, which is a continuation-in-part of Ser. No. 374,598, Jun. 28, 1973, abandoned.

[51] Int. Cl.² ........................ A01N 9/12; A01N 9/00
[52] U.S. Cl. ............................................. 71/90; 71/88
[58] Field of Search ..................................... 71/90, 88

[56] References Cited

U.S. PATENT DOCUMENTS

| 3,565,901 | 2/1971 | Cebalo | 71/90 |
| 3,726,892 | 4/1973 | Cebalo | 71/90 |
| 3,824,247 | 7/1974 | Doyle, Jr. et al. | 71/90 |
| 4,021,225 | 5/1977 | Hedrich et al. | 71/90 |

OTHER PUBLICATIONS

Wicks et al., "Chemical Fallow in a Winter Wheat, etc.," Weed Sci. 21, pp. 97–102 (1973).
Burnside et al., "Weed Control in Winter Wheat, etc.," Weed Sci. 16, pp. 255–258 (1968).

*Primary Examiner*—Glennon H. Hollrah
*Attorney, Agent, or Firm*—Dwight E. Morrison; Arthur R. Whale

[57] ABSTRACT

There is disclosed a method of controlling unwanted vegetation in fallow wheatland by the application of a substituted thiadiazol-2-ylurea following the harvesting of the wheat crop.

8 Claims, No Drawings

HERBICIDAL METHOD

CROSS REFERENCE

This application is a continuation-in-part of my copending application Ser. No. 683,872, filed May 6, 1976, now abandoned, which was a continuation-in-part of application Ser. No. 533,897, filed Dec. 18, 1974, now U.S. Pat. No. 3,972,706, which was a continuation of my then copending application Ser. No. 374,598, filed June 28, 1973, now abandoned.

BACKGROUND OF THE INVENTION

1. Field of the Invention

In those sections of the country wherein total rainfall amounts to as little as 10 to 20 inches per year, in order to raise winter wheat satisfactorily, it is necessary to allow the land to lie fallow, that is, to remain unplanted during the year following the harvest of a crop of winter wheat, which harvest usually occurs in July or August. The main purpose of the practice is to conserve what moisture is provided by nature. Best results from the conservation of moisture standpoint are obtained by preventing the growth of weeds and volunteer winter wheat between the time of harvest in one year (that is, in July or August) and the time of planting the seed for the new crop of winter wheat approximately a year later, in September or October.

In those sections of the country where, because of the sparcity of rainfall, a fallow-land program must be followed in order to raise spring wheat, the wheat crop is harvested in about August. The land then is allowed to lie fallow through the suceeding fall and winter months, and through the spring, summer, fall, and winter months of the succeeding year, and then in the spring of the next year, the seed for the new crop of spring wheat is planted. Thus, there is a fallow period of about 18–22 months in the spring wheat fallow program.

The control of weeds which grow in wheat fields after the wheat crop has been harvested has long been a problem to wheat farmers. The growth of the weeds has several disadvantages. The weeds, by their presence and growth, take needed moisture and nutrients from the soil, and prevention of this loss of moisture is particularly important in winter wheat production because of the relative scarcity of rainfall in those regions where winter wheat is grown. Further, the weeds are of no use as fodder for the farm animals. When the weeds mature, the seeds which are produced at maturity are scattered by the winds, birds, and animals, so that the infestation of weeds spreads far beyond the confines of the particular field.

2. Description of the Prior Art

The usual method of controlling the weeds in fallow wheatland has been to plow the field periodically, or otherwise cultivate the field to kill the weeds. These operations kill the weeds so they do not mature and produce additional seeds, and so that the depletion of water in the soil by the weeds is prevented. The plowing and other cultivations do make the soil more friable and more receptive to rainfall, and the rainwater thereby does not run off and become lost.

However, the disadvantages of the usual method of controlling weeds in fallow wheatland are of such significance they are not to be overlooked. Control of the weeds by plowing usually requires above five plowings between the time of harvesting the wheat one year and the seeding of the new crop approximately one year later in the case of winter wheat, or about 18–22 months later in the case of spring wheat. Such plowing take time to accomplish. There is wear and tear on the machinery used by the wheat producer to accomplish the cultivations. The multiple cultivations also loosen the soil and thus permit greater wind erosion of the soil. In addition, there is the increased consumption of fuel to power the machinery used in the cultivations. There would thus be significant overall savings to the producer, together with benefit to the ecology, if the number of man and machine operations on the soil could be reduced.

While the prior art refers to many thiadiazoles and derivatives thereof, none of the prior art is believed to be an enabling disclosure of the specific use disclosed and claimed herein. Some related compounds shown in the prior art, such as, for example, 1-(5-methyl-1,3,4-thiadiazol-2-yl)-3-phenylthiourea and 1-(5-methyl-1,3,4-thiadiazol-2-yl)-3-phenylurea [*J. Pharm. Soc.*, Japan 74, 1044–1048, (1954); C.A. 49, 11630 (1955)], were not reported to have biological activity.

An article in *Farmaco Ed. Sci.* 22 (6), 393–401 (1967), discloses the use of 1-(5-alkyl-1,3,4-thiadiazol-2-yl)ureas as intermediates for the production of isomeric 1,3-bis-(5-alkyl-1,3,4-thiadiazol-2-yl)ureas, which latter compounds are alleged to exhibit hypoglycemic action. These compounds are only generally related to those used in the practice of the instant invention.

In U.S. Pat. No. 3,565,901 (Feb. 23, 1971), are taught salts of certain thiadiazol-2-ylureas alleged to be useful in agricultural applications as phytotoxicants. These salts are formed by thiadiazol-2-ylureas unsubstituted on the urea nitrogen closest to the thiadiazole ring. There is no mention of possible utility of the compounds in the cultivation of winter or spring wheat, and no test data regarding safety to winter or spring wheat.

Belgian Patent No. 765,930, teaches the use of 1,3-dimethyl-1-(5-tert.-butyl-1,3,4-thiadiazol-2-yl)urea, and 1-ethyl-1-(5-tert.-butyl-1,3,4-thiadiazol-2-yl)-3-methylurea, as pre- and postemergence herbicides on plant crops such as corn, cotton, peanuts, sorghum, and sugarcane. Data in this Belgian patent show that corn, cotton, sorghum, and wheat are largely destroyed by either pre- or postemergence application of from about 1.12 to about 5.6 kg./ha. of 1,3-dimethyl-3-(5-t-butyl-1,3,4-thiadiazol-2-yl)urea, or 1-ethyl-1-(5-t-butyl-1,3,4-thiadiazol-2-yl)-3-methylurea. The Belgian patent makes no suggestion that modification of the therein disclosed compounds to the structures disclosed in the instant application would yield compounds useful in the control of weeds in fallow wheatland.

In addition, Belgian Patent Specification No. 744,812, teaches substituted 1,3,4-thiadiazoles, and alleges their utility as preemergence and/or postemergence herbicides, and as defoliants and dessicants of plants. No teaching of utility as selective herbicides appear to be present.

British Patent Specification No. 1,195,672, published June 17, 1970, teaches thiadiazoles alleged to possess utility as pre- and/or postemergence herbicides, together with herbicidal compositions containing the thiadiazoles as active ingredient, and a method of controlling plant growth. No suggestion that any of the compounds would be suitably selective for use as herbicides in the cultivation of winter wheat is present and winter wheat is not mentioned in the patent.

Yet another British Patent Specification No. 1,230,432, published May 5, 1971, is concerned with N-substituted 5-amino-1,3,4-thiadiazoles, the processes for their production, and their use as herbicides. A number of plants, including cotton, carrots, coffee, beans, beets, sugarcane, potatoes, bluegrass, barley, and wheat, as well as mustard, common chickweed, fescue, foxtail, and the like, are listed as susceptible to control by the N-substituted thiadiazoles. Thus, the control of desirable crop plants is made synonymous with the control of weed plants.

Another reference, British Patent Specification No. 1,254,468, published Nov. 24, 1971, is directed to 5-substituted 1,3,4-thiadiazolylureas, to processes for the production thereof, and to herbicidal compositions containing the named compounds. Utility for the control of weeds and wild grasses is alleged. No teaching is present of possible selectivity of herbicidal action of the compounds, nor utility in the cultivation of winter or spring wheat.

British Patent Specification No. 1,266,172, published Mar. 8, 1972, is directed to substituted thiadiazole compounds and alleges their utility as herbicides, fungicides, acaricides, or insecticides. There is no allegation in the British patent that the compounds listed therein would be useful as herbicides in the cultivation of winter or spring wheat.

Kubo et al., *J. Agr. Food Chem.* 18 (1) 60–65 (1970), teach the results of the study of the preemergence and postemergence herbicidal activity of a number of 1-substituted-3-(5-substituted-1,3,4-thiadiazol-2-yl)ureas. The compound, 1-methyl-3-(5-t-butyl-1,3,4-thiadiazol-2-yl)urea, is reported as a strikingly phytotoxic compound. These authors report that this compound completely killed wheat when applied at the rate of 5 kg./ha. postemergence, but that it caused only slight damage to the wheat when applied at the same rate preemergence the day the seed was planted. However, preemergence tests in our laboratories using this compound at rates of 1.12, 2.24, and 4.48 kg./ha. killed the wheat.

Also in the prior art is British Patent Specification No. 1,297,147, published Nov. 22, 1972, which teaches 1,3,4-thiadiazolyl-(5)-ureas and their use as pre- or postemergence herbicides. The compounds are alleged to be particularly well suited for selective weed control in cereals, cotton, and carrots. In general, the application rate is taught as being from 1 to 50 kg./ha., preferably from 2 to 20 kg./ha. There is no teaching or disclosure suggesting use on fallow wheatland in the cultivation of winter or spring wheat. In general, with few exceptions, the compounds tested killed wheat plants when applied either pre- or postemergent, according to the data disclosed in the patent.

Another prior art reference is U.S. Pat. No. 3,726,892 (Apr. 10, 1973), directed to thiadiazol-2-ylureas containing a sulfonamido group in the 5-position. The compounds are alleged to be active as agricultural pesticides, particularly herbicides. There is no teaching that the compounds taught therein would be usable in the cultivation of wheat in a fallow wheatland program.

Another prior art reference is Eue et al., entitled "A New Total Herbicide of the Thiadiazole Base," *Proc. 7th C.O.L.U.M.A. Conference*, Versailles, France, Dec. 13–14th, 1973, Vol. I, pp. 14–22. This reference teaches that 3-(5-ethylsulfonyl-1,3,4-thiadiazol-2-yl)-1,3-dimethylurea is an excellent total herbicide, having very long activity and extremely broad activity, when applied either pre- or postemergence. The compound is only recommended for use on roads, railroad tracks, and industrial sites. The authors teach that use of the compound for selective weed control in crops is not possible.

Yet another prior art reference is Muller et al., entitled "1,3-Dimethyl-3-(5-trifluoromethyl-1,3,4-thiadiazolyl-(2))-urea, A New Substance for Total Weed Control," *Proc. 7th C.O.L.U.M.A. Conference*, Versailles, France, Dec. 13–14th, 1973, Vol. I, pp. 22–32. The reference teaches the compound is reserved for purely "industrial" weed control where long lasting activity and total weed control is desired. The compound shows a long and nonspecific efficacy against a wide range of mono- and dicotyledons, including shrubs and bushes, according to the reference. There is no teaching that modification of the disclosed compound to the structures of the instant application would make such compounds useful in fallow wheatland weed control.

The search continues for a satisfactory method of controlling the growth of unwanted vegetation in fallow winter or spring wheatland, which method reduces the need to cultivate the land numerous times.

SUMMARY OF THE INVENTION

It is an object of this invention to provide methods for controlling unwanted vegetation in fallow wheatland.

In fulfillment of this object, this invention provides a novel method which comprises applying to a field from which the wheat has been harvested, an herbicidally-effective amount of one or more thiadiazolylurea derivatives.

DETAILED DESCRIPTION OF THE INVENTION

This invention relates to novel methods for the control of unwanted vegetation. More particularly, this invention relates to novel herbicidal methods for the control of unwanted vegetation in fallow wheatland, in which herbicidal methods the herbicidal compound has the formula

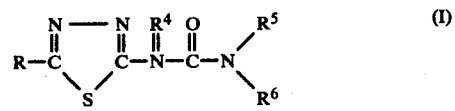

wherein

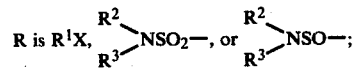

$R^1$ is lower alkyl or $C_3$–$C_7$ cycloalkyl;
X is —S—,

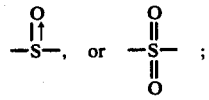

$R^2$ is hydrogen or a substituted or unsubstituted lower alkyl, the substituents being selected from the class consisting of halo, hydroxy, cyano, and lower alkoxy;

$R^3$ is lower alkoxy, lower alkenyl, lower alkynyl, or a substituted or unsubstituted lower alkyl, the substituents being selected from the class consisting of halo, hydroxy, cyano, and lower alkoxy;

$R^2$ and $R^3$, when taken together with the nitrogen to which they are attached, form a morpholino, piperidino, or pyrrolidino group;

$R^4$ is hydrogen or lower alkyl;

$R^5$ is hydrogen, lower alkyl, lower alkenyl, or $C_3$-$C_7$ cycloalkyl;

$R^6$ is hydrogen, lower alkenyl, $C_3$-$C_7$ cycloalkyl, lower alkoxy, or a substituted or unsubstituted lower alkyl, the substituents being selected from the group consisting of halo, hydroxy, cyano, or lower alkoxy, except that $R^5$ and $R^6$ cannot both be hydrogen or a $C_3$-$C_7$ cycloalkyl; and tautomers of (I) wherein $R^4$ is hydrogen; and when $R^4$ is hydrogen, the alkali metal, alkaline earth metal and ammonium salts thereof.

The compounds preferred for use in the novel method of this invention are of the formula $$R-C\underset{S}{\overset{N-N}{\|\ \|}}C-N-\underset{}{\overset{R^4}{|}}\overset{O}{\overset{\|}{C}}-N\underset{R^6}{\overset{R^5}{\diagup}} \quad (I)$$

wherein

R is $R^1X$ or $\underset{R^3}{\overset{R^2}{\diagdown}}NSO_2-$;

$R^1$ is lower alkyl or $C_3$-$C_7$ cycloalkyl;

X is —S— or $$-\underset{\underset{O}{\|}}{\overset{\overset{O}{\|}}{S}}-;$$

$R^2$ is hydrogen or a substituted or unsubstituted lower alkyl, the substituents being selected from the class consisting of halo, hydroxy, cyano, and lower alkoxy;

$R^3$ is lower alkoxy, lower alkenyl, lower alkynyl, or a substituted or unsubstituted lower alkyl, the substituents being selected from the class consisting of halo, hydroxy, cyano, and lower alkoxy; $R^4$ is hydrogen or lower alkyl;

$R^5$ is hydrogen, lower alkyl, lower alkenyl, or $C_3$-$C_7$ cycloalkyl;

$R^6$ is hydrogen, lower alkenyl, $C_3$-$C_7$ cycloalkyl, lower alkoxy, or a substituted or unsubstituted lower alkyl, the substituents being selected from the group consisting of halo, hydroxy, cyano, or lower alkoxy, except that $R^5$ and $R^6$ cannot both be hydrogen or a $C_3$-$C_7$ cycloalkyl; and tautomers of (I) wherein $R^4$ is hydrogen; and when $R^4$ is hydrogen, the alkali metal, alkaline earth metal and ammonium salts thereof.

The more preferred compounds for use in the novel method of this invention are of the formula $$\underset{R^3}{\overset{R^2}{\diagdown}}NSO_2-C\underset{S}{\overset{N-N}{\|\ \|}}C-N-\overset{\overset{O}{\|}}{C}-N\underset{R^6}{\overset{R^5}{\diagup}} \quad (II)$$

wherein $R^2$ is unsubstituted lower alkyl;

$R^3$ is lower alkenyl, lower alkynyl, or a substituted or unsubstituted lower alkyl, the substituents being selected from the class consisting of chloro, bromo, and lower alkoxy;

$R^4$ is hydrogen or lower alkyl;

$R^5$ is hydrogen or lower alkyl;

$R^6$ is lower alkyl; and, tautomers of (II) wherein $R^4$ is hydrogen; and when $R^4$ is hydrogen, the alkali metal, alkaline earth metal and ammonium salts thereof.

The compounds of choice are 1-(5-dimethylsulfamoyl-1,3,4-thiadiazol-2-yl)-1-ethyl-3-methylurea, and 1-(5-dimethylsulfamoyl-1,3,4-thiadiazol-2-yl)-1,3-dimethylurea.

In the above formulas, alkyl and lower alkyl mean straight or branched chain $C_1$-$C_7$ alkyl, such as methyl, ethyl, n-propyl, isopropyl, n-butyl, sec.-butyl, t-butyl, n-pentyl, 2-pentyl, 3-pentyl, 2-methyl-2-butyl, n-hexyl, 2-hexyl, 3-hexyl, 1,1-dimethylpropyl, 3-methyl-3-pentyl, n-heptyl, 2-heptyl, 3-heptyl, 4-heptyl, 1,1-dimethylbutyl, and the like.

Lower alkynyl means $C_3$-$C_7$ alkynyl, such as 1-propynyl, 1-butynyl, 2-butynyl, 1-pentynyl, 2-pentynyl, 1-hexynyl, 2-hexynyl, 1-heptynyl, 2-heptynyl, and the like.

Lower alkenyl means $C_2$-$C_7$ alkenyl, illustratively, vinyl, allyl, 1-propenyl, crotyl, 2-methylallyl, 3-pentenyl, 5-hexenyl, 1-methyl-3-hexenyl and the like.

$C_3$-$C_7$ Cycloalkyl refers to saturated cycloalkyl, and means cyclopropyl, cyclobutyl, cyclopentyl, cyclohexyl, and cycloheptyl, respectively.

Lower alkoxy means $C_1$-$C_4$ alkoxy and includes methoxy, ethoxy, n-propoxy, isopropoxy, n-butoxy, isobutoxy, sec.-butoxy, or t-butoxy.

Halo means bromo, chloro, and fluoro.

Alkali and alkaline earth metals refers to sodium, potassium, lithium, strontium, calcium, barium, magnesium, and includes any monovalent or polyvalent metal which will form a thiadiazolylurea derivative having salt-like or chelate characteristics.

Ammonium refers to unsubstituted ammonium.

Compounds coming within the scope of the generic formula (I), supra, include, but are not limited to the following:

1,3-Dimethyl-3-(5-methylsulfonyl-1,3,4-thiadiazol-2-yl)urea
1,3-Dimethyl-3-(5-butylthio-1,3,4-thiadiazol-2-yl)urea
1,3-Dimethyl-3-(5-butylsulfonyl-1,3,4-thiadiazol-2-yl)urea
1-Methyl-1-methoxy-3-(5-methylthio-1,3,4-thiadiazol-2-yl)urea
1-Methyl-1-methoxy-3-(5-methylsulfonyl-1,3,4-thiadiazol-2-yl)urea
1-Butyl-1-methyl-3-(5-methylthio-1,3,4-thiadiazol-2-yl)urea
1-Butyl-1-methyl-3-(5-methylsulfonyl-1,3,4-thiadiazol-2-yl)urea
1,1-Dimethyl-3-ethyl-3-[5-(dimethylsulfamoyl)-1,3,4-thiadiazol-2-yl]urea
1,3-Dimethyl-3-[5-(methylsulfamoyl)-1,3,4-thiadiazol-2-yl]urea
1,3-Dimethyl-3-[5-(dimethylsulfamoyl)-1,3,4-thiadiazol-2-yl]urea
1,1,3-Trimethyl-3-[5-(dimethylsulfamoyl)-1,3,4-thiadiazol-2-yl]urea 1,1-Dimethyl-3-ethyl-3-[5-(dimethylaminosulfinyl)-1,3,4-thiadiazol-2-yl]urea 1,3-Dimethyl-3-[5-(methylaminosulfinyl)-1,3,4-thiadiazol-2-yl]urea 1,1,3-Trimethyl-3-[5-(dimethylaminosulfinyl)-1,3,4-thiadiazol-2-yl]urea 1-Butyl-1-methyl-3-(5-dimethylsulfamoyl-1,3,4-thiadiazol-2-yl)urea 1-Cyclopropyl-3-(5-dimethylsulfamoyl-1,3,4-thiadiazol-2-yl)urea 1-Methyl-3-(5-morpholinosulfamoyl-1,3,4-thiadiazol-2-yl)urea 1,3-Dimethyl-3-(5-dimethylsulfamoyl-1,3,4-thiadiazol-2-yl)urea 1-Methyl-1-methoxy-3-(5-dimethylsulfamoyl-1,3,4-thiadiazol-2-yl)urea 1-Methyl-3-(5-N-butyl-N-methylsulfamoyl-1,3,4-thiadiazol-2-yl)urea 1-Methyl-3-(5-N-butylsulfamoyl-1,3,4-thiadiazol-2-yl)urea 1-Methyl-3-(5-N,N-dipropylsulfamoyl-1,3,4-thiadiazol-2-yl)urea 1-Methyl-3-(5-N-allylsulfamoyl-1,3,4-thiadiazol-2-yl)urea, and the like.

It has been found that when a thiadiazol-2-ylurea coming within the scope of the above structural formula (I) is applied to the soil at a rate of from about 0.56 to about 2.2 kg./ha., preferably at a rate of from about 0.56 to about 1.1 kg./ha., after the wheat has been harvested, almost complete control is obtained of the undesirable weeds and grasses which usually grow on fallow wheatland between the time of the wheat harvest in one year and the time of planting the winter wheat approximately a year later, or the planting of spring wheat about 18–22 months later.

This control is accomplished without the necessity of the five or more plowings or cultivations usually required to destroy the unwanted vegetation and to prevent the loss of moisture from the soil caused by the growth of the unwanted vegetation. Thus, the number of plowings or cultivations of the field is reduced to about two, producing a large saving in time and effort for the wheat grower. The reduction in the number of cultivations also decreases the chances of wind erosion of the loosened soil. The amount of fuel needed to power the machinery is decreased, as well as the wear and tear on the machinery.

In one embodiment of the invention, the thiadiazol-2-ylurea is applied to the field of wheat stubble within a few weeks of the harvesting of the wheat. Ideally, in the case of winter wheat, the land will then remain undisturbed during the winter, the following spring, and the following summer. Any weed not completely destroyed or controlled by the thiadiazolylurea can be controlled by one or two cultivations, or by application of short-term, non-persistent herbicides. At such time that is necessary, the stubble ground is plowed, disced or undercut, which is the first step in preparing the soil for seeding to winter wheat in the fall. In the case of spring wheat, the land will remain undisturbed during the winter, the following spring, the following summer and fall, and through the second winter. Any weeds not completely destroyed or controlled by the thiadiazolylurea can be controlled by one or two cultivations, or by application of short-term, non-persistent herbicides. At such time that is necessary during the second spring, the stubble ground is plowed, disced, or is undercut, which is the first step in preparing the soil for seeding to spring wheat during the spring.

In a second embodiment of the invention, the thiadiazol-2-ylurea is applied about 8 or 9 months after the harvest of the wheat, that is, in about March or April in the spring of the year following the wheat harvest. In this embodiment, the wheat stubble may be undercut soon after the harvest, and the herbicide applied about 8 or 9 months later.

In either embodiment, the winter wheat or the spring wheat is then planted at the normal and usually scheduled time. Prior to planting, the field is prepared to receive the wheat seed.

The usual and customary procedure for preparing the land for planting of the wheat understandably varies in different portions of the country, due both to the type of soil and to the farming customs of the various areas of the country.

It is recognized that the herbicidal activity of the compounds coming within the scope of generic formula (I) supra, will vary depending on the substituents attached to the basic thiadiazolylurea molecule, and those skilled in the art will be able to select from the disclosed compounds the ones suitable for controlling the unwanted vegetation in fallow wheat land for the period of time desired.

Thus, it is known to those skilled in the art that those thiadiazol-2-ylureas bearing an alkyl substituent on the urea nitrogen nearest the thiadiazole ring are more persistent and longer acting herbicides than those thiadiazol-2-ylureas bearing only a hydrogen substituent on the urea nitrogen nearest the thiadiazole ring. Use of this knowledge of variation in persistence of the compounds can therefore be made in selecting the thiadiazol-2-ylureas for use in the winter wheat fallow and spring wheat fallow programs depending on the length of the fallow period and the length of time it is desired that the herbicide persist.

The weeds which it has been found possible to control by this novel method include, but are not limited to the following: witchgrass (*Panicum capillare*), Russian thistle (*Salsola kali*), Kochia or Mexican fireweed (*Kochia scoparia*), pigweed (Amaranthus sp.), as well as stink grass or love grass (*Eragrostis cilianensis*), downy bromegrass (*Bromus tectorum*), wild mustard (*Brassica kaber*), sunflower (*Helianthus annuus*), lambsquarter (*Chenopodium album*), and volunteer wheat (Triticum sp.).

The compounds useful in the novel herbicidal process of this invention may be prepared by methods which are normally employed for the synthesis of urea derivatives and which are well documented in the chemical literature.

Those compounds having an alkylthio or an alkylsulfonyl substituent in the 5-position of the thiadiazole, and useful in the novel herbicidal process of this invention can be prepared by one or more of the synthesis routes set forth below. The type of product desired will determine the particular synthesis route to be employed.

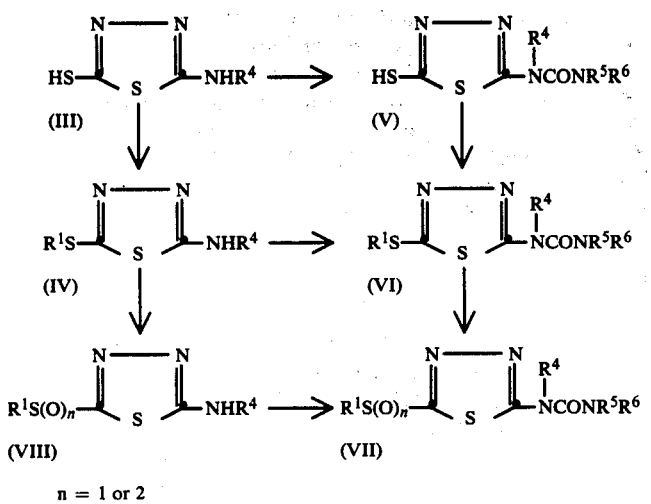

n = 1 or 2

The intermediate compositions corresponding to Structure (III) are synthesized by methods known in the art. For example, such methods are generally taught in publications such as *The Chemistry of Heterocyclic Compounds* V. 4, L. L. Bambas, Interscience Publishers, Inc., New York, 1952 and Petrow et al., *J. Chem. Soc.* 1508 (1958). The compounds having the Structure (IV) and (VI) may be synthesized from compounds (III) and (V) by known methods, e.g. reacting compounds (III) and (V) with alkyl halides and dialkyl sulfates in the presence of a base such as potassium carbonate, sodium hydroxide, potassium hydroxide and the like.

Compounds having the ureido moieties, as shown above, may be synthesized by reactions which are known in the art. It is understood that the method employed will depend upon the particular intermediate selected for producing the corresponding intermediate or desired final product.

The alkylmercapto compounds of structure (VI) may be oxidized to the corresponding sulfones of structures (VII) and (VIII) by oxidizing reagents such as chlorine-acetic acid, chlorine-ferric chloride, potassium permanganate, hydrogen peroxide-acetic acid and the like. By careful control of oxidizing conditions, the sulfoxides of structures (VII) and (VIII) are also prepared.

The following examples are illustrative of the methods of preparation of various compounds for use in the novel herbicidal method of this invention.

EXAMPLE 1

A mixture containing 30 g. of 2-(N-methylamino)-5-mercapto-1,3,4-thiadiazole and 11.60 g. of methyl isocyanate in 250 ml. of benzene was refluxed in a 500 ml. flask for a period of about 2 hours. The reaction product mixture was cooled and filtered to obtain 40 g. of a product having a melting point of about 162°–164° C., and identified as 1,3-dimethyl-3-(5-mercapto-1,3,4-thiadiazol-2-yl)urea.

Following the same general procedure of Example 1, and using suitable starting reactants, additional compounds were prepared.

A. Methyl isocyanate was allowed to react with 2-(N-methylamino)-5-butylmercapto-1,3,4-thiadiazole to yield 1,3-dimethyl-2-(5-butylmercapto-1,3,4-thiadiazol-2-yl)urea, having a melting point of about 63°–65° C.

EXAMPLE 2

A mixture containing 5 g. of 1,3-dimethyl-3-(5-mercapto-1,3,4-thiadiazol-2-yl)urea, 3.7 g. of methyl iodide, and 1.7 g. of anhydrous potassium carbonate in 50 ml. of N,N-dimethylformamide, was stirred for about 15 hours at a temperature of about 70° C. The resulting clear reaction product mixture was concentrated under vacuum to a solid, which solid, on recrystallization from ethyl acetate, yielded a product identified as 1,3-dimethyl-3-(5-methylmercapto-1,3,4-thiadiazol-2-yl)urea, having a melting point of about 154°–156° C.

EXAMPLE 3

To a suspension of 5 g. of 1,3-dimethyl-3-(5-methylmercapto-1,3,4-thiadiazol-2-yl)urea in 50 ml. of acetic acid was added, dropwise and with stirring, an aqueous solution of potassium permanganate (7.3 g. in 100 ml. of water), said reaction mixture being cooled in an ice water bath. The resulting mixture was stirred for about 15 hours at room temperature after which time sodium bisulfite was added until the mixture became colorless. The solid product was filtered off, and was recrystallized from methanol to yield a product identified as 1,3-dimethyl-3-(5-methylsulfonyl-1,3,4-thiadiazol-2-yl)urea, having a melting point of about 182°–183° C.

EXAMPLE 4

In a three-necked round-bottom flask equipped with a mechanical stirring means and bubbling tube were placed 35.9 g. of 1,3-dimethyl-3-(5-butylmercapto-1,3,4-thiadiazol-2-yl)urea and 5 g. of ferric chloride hexahydrate in 500 ml. of water. The mixture was cooled to 5° C. and a steady stream of chlorine was bubbled through the mixture for about 20 minutes while maintaining the temperature at 7°–9° C. Nitrogen was subsequently bubbled through the mixture to remove excess chlorine. The reaction product mixture was filtered and the solid product recrystallized from aqueous methanol to provide a product identified as 1,3-dimethyl-3-(5-butylsulfonyl-1,3,4-thiadiazol-2-yl)urea, having a melting point of about 123°–124° C.

EXAMPLE 5

To a stirred solution containing 10 g. of N,N'-carbonyldiimidazole in 200 ml. of dry tetrahydrofuran was added 9.1 g. of 2-amino-5-methylmercapto-1,3,4- thiadiazole, the mixture being stirred for an additional 30 minutes under a nitrogen atmosphere and subsequently refluxed. The reaction mixture was cooled to room temperature and 18.7 g. of triethylamine was added followed by 18.0 g. of dimethyl hydroxylamine hydrochloride. After stirring for 15 minutes, the reaction product mixture was poured into an ice and water mixture and extracted with ethyl acetate. The ethyl acetate extract was dried over anhydrous sodium sulfate and subsequently concentrated under vacuum to a residual oil which solidified on standing. The solid material was recrystallized from methanol to yield a crystalline product which was identified as 1-methyl-1-methoxy-3-(5-methylmercapto-1,3,4-thiadiazol-2-yl)urea, having a melting point of about 97°–100° C.

EXAMPLE 6

To a stirred solution containing 10.1 g. of 1-methyl-1-methoxy-3-(5-methylmercapto-1,3,4-thiadiazol-2-yl)urea and 50 g. of glacial acetic acid, heated to 85°–90° C., was added, over a period of about 15 minutes, 14.5 g. of 30 percent hydrogen peroxide. The temperature was maintained for an additional period of one hour and the mixture was then cooled to room temperature. The cooled reaction product mixture was poured into an ice and water mixture and extracted with ethyl acetate. The ethyl acetate extract was dried over anhydrous sodium sulfate and concentrated under vacuum to yield a product identified as 1-methyl-1-methoxy-3-(5-methylsulfonyl-1,3,4-thiadiazol-2-yl)urea, having a melting point of about 146°–148° C.

Following the same general procedure of Example 6, the following additional compound was prepared and identified. The compound, together with the principle starting materials and weights thereof used in its preparation, is listed in the example set forth hereinafter.

A. 1,1-Dimethyl-3-[5-(methylsulfonyl)-1,3,4-thiadiazol-2-yl]urea, having a melting point of about 194°–195° C., and weighing 0.5 g., from 1.1 g. of 1,1-dimethyl-3-(5-methylmercapto-1,3,4-thiadiazol-2-yl)urea and 1.1 g. of 30 percent hydrogen peroxide.

Analyses calculated for $C_6H_{10}N_4O_3S_2$:

|   | Theoretical | Found |
|---|---|---|
| C | 28.79% | 28.91% |
| H | 4.03 | 3.79 |
| N | 22.38 | 22.12 |

EXAMPLE 7

To a well-stirred mixture of 20 g. of 2-amino-5-methylmercapto-1,3,4-thiadiazole and 18.4 g. of N-methyl-N-butylcarbamoyl chloride, in dimethylformamide, which mixture had been cooled to about 5° C., was slowly added 4.7 g. of sodium hydride. The reaction mixture was slowly poured into an ice and water mixture and the total mixture extracted with chloroform. The chloroform extract was concentrated under vacuum to yield a material which, on recrystallization from ethanol, provided a product identified as 1-butyl-1-methyl-3-(5-methylmercapto-1,3,4-thiadiazol-2-yl)urea, having a melting point of about 93°–94° C.

EXAMPLE 8

A stirred mixture, containing 9.3 g. of 1-butyl-1-methyl-3-(5-methylmercapto-1,3,4-thiadiazol-2-yl)urea and 5.0 g. of ferric chloride in 400 ml. of water, was cooled to about 5° C., and chlorine gas was bubbled through the mixture for about 30 minutes. Nitrogen was then bubbled through the mixture to remove excess chlorine and the precipitate which formed was obtained by filtering the solution. The precipitate was recrystallized from ethyl alcohol to yield a product which was identified as 1-butyl-1-methyl-3-(5-methylsulfonyl-1,3,4-thiadiazol-2-yl)urea, having a melting point of about 125°–126° C.

The compounds wherein

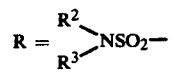

can be synthesized by reaction sequences taught by Cebalo, U.S. Pat. No. 3,726,892 (Apr. 10, 1973), the disclosures of which patent are hereby incorporated into and made a part of this specification.

EXAMPLE 9

Following the general procedure of Example 7, 2-methylamino-1,3,4-thiadiazolo-5-N,N-dimethylsulfonamide was allowed to react with N,N-dimethylcarbamoyl chloride to yield 1,1,3-trimethyl-3-(5-dimethylsulfamoyl-1,3,4-thiadiazol-2-yl)urea, having a meltling point of about 101°–103° C.

Following the general procedure of Example 9, the following additional compounds were prepared.

A. 2-Ethylamino-1,3,4-thiadiazole-5-N,N-dimethylsulfonamide was allowed to react with N,N-dimethylcarbamoyl chloride to yield 1,1-dimethyl-3-ethyl-3-(5-dimethylsulfamoyl-1,3,4-thiadiazol-2-yl)urea, having a melting point of about 75°–77° C.

B. 1-[5-(N-Ethyl-N-methylsulfamoyl)-1,3,4-thiadiazol-2-yl]-1,3,3-trimethylurea, as an oil, and weighing 1.2 g. from 6 g. of 2-methylamino-1,3,4-thiadiazole-5-(N-ethyl-N-methyl)sulfonamide and 4.2 g. of N,N-dimethylcarbamoyl chloride.

Analyses calculated for $C_9H_{17}N_5O_3S_2$:

|   | Theoretical | Found |
|---|---|---|
| C | 35.17% | 35.37% |
| H | 5.57 | 5.60 |
| N | 22.78 | 22.60 |

C. 1-[5-[N-(2,2-Dimethoxyethyl)-N-methylsulfamoyl]-1,3,4-thiadiazol-2-yl]-1,3,3-trimethylurea, having a melting point of about 78°–79° C., and weighing 3 g., from 2-methylamino-1,3,4-thiadiazole-5-[N-(2,2-dimethoxyethyl)-N-methyl]sulfonamide and 2.2 g. of dimethylcarbamoyl chloride.

Analyses calculated for $C_{11}H_{21}N_5O_5S_2$:

|   | Theoretical | Found |
|---|---|---|
| C | 35.96% | 36.23% |
| H | 5.76 | 5.93 |
| N | 19.06 | 19.20 |

D. 1,1,3-Trimethyl-3-[5-[N-(s-butyl)-N-methylsulfamoyl]-1,3,4-thiadiazol-2-yl]urea, having a melting point of about 60°–62° C., and weighing 0.2 g., from 5.28 g. of 2-methylamino-1,3,4-thiadiazole-5-(N-s-butyl-N-methyl)sulfonamide and 2.15 g. of dimethylcarbamoyl chloride.

Analyses calculated for $C_{11}H_{21}N_5O_3S_2$:

|   | Theoretical | Found |
|---|---|---|
| C | 39.39% | 39.59% |
| H | 6.31 | 6.61 |
| N | 20.88 | 20.72 |

E.    1-[5-(N-Isobutyl-N-methylsulfamoyl)-1,3,4-thiadiazol-2-yl]-1,3,3-trimethylurea, as an oil, and weighing 4 g., from 5.8 g. of 2-methylamino-1,3,4-thiadiazole-5-(N-isobutyl-N-methyl)sulfonamide and 3.0 g. of dimethylcarbamoyl chloride.

Analyses calculated for $C_{11}H_{21}N_5O_3S_2$:

|   | Theoretical | Found |
|---|---|---|
| C | 39.39% | 39.64% |
| H | 6.31 | 6.06 |
| N | 20.88 | 20.54 |
| S | 19.12 | 19.25 |

EXAMPLE 10

Following the general procedure of Example 1, 2-ethylamino-1,3,4-thiadiazole-5-(N-methyl-N-methallyl)sulfonamide, 7 g., was allowed to react with 5 g. of methylisocyanate to yield 1-ethyl-3-methyl-3-[5-[N-methyl-N-(2-methallyl)sulfamoyl]-1,3,4-thiadiazol-2-yl]urea, weighing 4.9 g., and having a melting point of about 65°–66° C.

Analyses calculated for $C_{11}H_{19}N_5O_3S_2$:

|   | Theoretical | Found |
|---|---|---|
| C | 39.62% | 39.55% |
| H | 5.74 | 5.49 |
| N | 21.00 | 20.76 |
| S | 19.23 | 19.36 |

Additional compounds were prepared following the same general procedure of Example 10. The compounds, together with the principal starting materials and weights thereof used in the syntheses, are set forth hereinafter. The compounds were identified by melting point, NMR spectrum and elemental analyses.

A.    1-[5-(N-Butyl-N-methylsulfamoyl)-1,3,4-thiadiazol-2-yl]-1-ethyl-3-methylurea, having a melting point of about 94°–95° C., and weighing 2.6 g., from 4 g. of 2-ethylamino-1,3,4-thiadiazole-5-(N-butyl-N-methyl)sulfonamide and 2 g. of methylisocyanate.

Analyses calculated for $C_{11}H_{21}N_5O_3S_2$:

|   | Theoretical | Found |
|---|---|---|
| C | 39.39% | 39.43% |
| H | 6.31 | 6.09 |
| N | 20.88 | 20.34 |
| S | 19.12 | 19.39 |

B.    1,3-Dimethyl-3-[5-[N-methyl-N-(2-propynyl)sulfamoyl]-1,3,4-thiadiazol-2-yl]urea, having a melting point of about 177°–178° C., and weighing 2.4 g., from 5 g. of 2-methylamino-1,3,4-thiadiazole-5-[N-methyl-N-(2-propynyl)]-sulfonamide and 3 g. of methylisocyanate.

Analyses calculated for $C_9H_{13}N_5O_3S_2$:

|   | Theoretical | Found |
|---|---|---|
| C | 35.63% | 35.43% |
| H | 4.32 | 4.41 |
| N | 23.09 | 22.84 |
| S | 21.14 | 21.42 |

C.    1-[5-(N-Ethyl-N-propylsulfamoyl)-1,3,4-thiadiazol-2-yl]-1,3-dimethylurea, having a melting point of about 159°–161° C., and weighing 525 mg., from 4.8 g. of 2-methylamino-5-(N-ethyl-N-propyl)sulfonamide and 2.5 g. of methylisocyanate.

Analyses calculated for $C_{10}H_{19}N_5O_3S_2$:

|   | Theoretical | Found |
|---|---|---|
| C | 37.37% | 37.23% |
| H | 5.96 | 5.75 |
| N | 21.79 | 21.82 |
| S | 19.95 | 20.21 |

D.    1-Ethyl-1-[5-(N-ethyl-N-methylsulfamoyl)-1,3,4-thiadiazol-2-yl]-3-methylurea, having a melting point of about 95°–96° C., and weighing 1.9 g., from 4 g. of 2-methylamino-1,3,4-thiadiazole-5-(N-ethyl-N-methyl)-sulfonamide and 2 g. of methylisocyanate.

Analyses calculated for $C_9H_{17}N_5O_3S_2$:

|   | Theoretical | Found |
|---|---|---|
| C | 35.17% | 35.24% |
| H | 5.57 | 5.33 |
| N | 22.78 | 22.83 |
| S | 20.86 | 20.81 |

E.    1-Ethyl-3-methyl-1-[5-(N-methyl-N-propylsulfamoyl)-1,3,4-thiadiazol-2-yl]urea, having a melting point of about 91°–92° C., and weighing 5.4 g., from 6 g. of 2-ethylamino-1,3,4-thiadiazole-5-(N-methyl-N-propyl)sulfonamide and 2 g. of methylisocyanate.

Analyses calculated for $C_{10}H_{19}N_5O_3S_2$:

|   | Theoretical | Found |
|---|---|---|
| C | 37.37% | 37.66% |
| H | 5.96 | 5.77 |
| N | 21.79 | 21.89 |
| S | 19.95 | 19.93 |

F.    1-Ethyl-1-[5-(N-isobutyl-N-methylsulfamoyl)-1,3,4-thiadiazol-2-yl]-3-methylurea, having a melting point of about 84°–87° C., then resolidifying and melting at about 114°–115° C., and weighing 5.1 g., from 5 g. of 2-ethylamino-1,3,4-thiadiazole-5-(N-isobutyl-N-methyl)sulfonamide and 2.5 g. of methylisocyanate.

Analyses calculated for $C_{11}H_{21}N_5O_3S_2$:

|   | Theoretical | Found |
|---|---|---|
| C | 39.39% | 39.24% |
| H | 6.31 | 6.12 |
| N | 20.88 | 20.80 |
| S | 19.12 | 19.23 |

G.    1-[5-(N-Allyl-N-methylsulfamoyl)-1,3,4-thiadiazol-2-yl]-1-ethyl-3-methylurea, having a melting point of about 120°–121° C., and weighing 4.9 g., from 7 g. of 2-ethylamino-1,3,4-thiadiazole-5-(N-allyl-N-methyl)sulfonamide and 5 g. methylisocyanate.

Analyses calculated for $C_{10}H_{17}N_5O_3S_2$:

|   | Theoretical | Found |
|---|---|---|
| C | 37.60% | 37.71% |
| H | 5.36 | 5.26 |
| N | 21.83 | 22.14 |
| S | 20.08 | 19.84 |

H. 1-[5-(N-Ethyl-N-methylsulfamoyl)-1,3,4-thiadiazol-2-yl]-1,3-dimethylurea, having a melting point of about 184°–186° C., and weighing 4.1 g., from 5 g. of 2-methylamino-1,3,4-thiadiazole-5-(N-ethyl-N-methyl)sulfonamide and 2.5 g. of methylisocyanate.

Analyses calculated for $C_8H_{15}N_5O_3S_2$:

|   | Theoretical | Found |
|---|---|---|
| C | 32.75% | 32.95 |
| H | 5.15 | 4.89 |
| N | 23.87 | 23.59 |

I. 1,3-Dimethyl-3-[5-(N-methyl-N-propylsulfamoyl)-1,3,4-thiadiazol-2-yl]urea, having a melting point of about 119°–121° C., and weighing 2.4 g., from 5 g. of 2-methylamino-1,3,4-thiadiazole-5-(N-methyl-N-propyl)sulfonamide and 2.5 g. of methylisocyanate.

Analyses calculated for $C_9H_{17}N_5O_3S_2$:

|   | Theoretical | Found |
|---|---|---|
| C | 35.17% | 35.00% |
| H | 5.57 | 5.29 |
| N | 22.78 | 22.88 |

J. 1-[5-(N,N-Diethylsulfamoyl)-1,3,4-thiadiazol-2-yl]-1,3-dimethylurea, having a melting point of about 197°–200° C., and weighing 1 g., from 3.5 g. of 2-methylamino-1,3,4-thiadiazole-5-(N,N-diethyl)sulfonamide and 3.5 g. of methylisocyanate.

Analyses calculated for $C_9H_{17}N_5O_3S_2$:

|   | Theoretical | Found |
|---|---|---|
| C | 35.17% | 35.36% |
| H | 5.57 | 5.73 |
| N | 22.78 | 22.49 |

K. 1-[5-(N-Butyl-N-methylsulfamoyl)-1,3,4-thiadiazol-2-yl]-1,3-dimethylurea, having a melting point of about 107°–109° C., and weighing 2.2 g., from 11 g. of 2-methylamino-1,3,4-thiadiazole-5-(N-butyl-N-methyl)sulfonamide and 3 g. of methylisocyanate.

Analyses calculated for $C_{10}H_{19}N_5O_3S_2$:

|   | Theoretical | Found |
|---|---|---|
| C | 37.37% | 37.15% |
| H | 5.96 | 5.75 |
| N | 21.79 | 21.64 |

L. 1-[5-(N-Allyl-N-methylsulfamoyl)-1,3,4-thiadiazol-2-yl]-1,3-dimethylurea, having a melting point of about 149°–150° C., and weighing 1.5 g., from 3 g. of 2-methylamino-1,3,4-thiadiazole-5-(N-allyl-N-methyl)sulfonamide and 1.5 g. of methylisocyanate.

Analyses calculated for $C_9H_{15}N_5O_3S_2$:

|   | Theoretical | Found |
|---|---|---|
| C | 35.40% | 35.62% |
| H | 4.95 | 4.76 |
| N | 22.93 | 22.75 |

M. 1-[5-[N-Ethyl-N-(2-methallyl)sulfamoyl]-1,3,4-thiadiazol-2-yl]-1,3-dimethylurea, having a melting point of about 141°–142° C., and weighing 1.2 g., from 3.5 g. of 2-methylamino-1,3,4-thiadiazole-5-[N-ethyl-N-(2-methallyl)]sulfonamide and 2 g. of methylisocyanate.

Analyses calculated for $C_{11}H_{19}N_5O_3S_2$:

|   | Theoretical | Found |
|---|---|---|
| C | 39.62% | 39.79% |
| H | 5.74 | 5.86 |
| N | 21.00 | 21.10 |
| S | 19.23 | 18.90 |

N. 1-[5-[N-(2-Chloroallyl)-N-methylsulfamoyl]-1,3,4-thiadiazol-2-yl]-1,3-dimethylurea, having a melting point of about 114°–116° C., and weighing 1.3 g., from 2.8 g. of 2-methylamino-1,3,4-thiadiazole-5-[N-(2-chloroallyl)-N-methyl]sulfonamide and 1.2 g. of methylisocyanate.

Analyses calculated for $C_9H_{14}N_5O_3S_2Cl$:

|   | Theoretical | Found |
|---|---|---|
| C | 31.81% | 31.77% |
| H | 4.15 | 3.98 |
| N | 20.61 | 20.43 |
| S | 18.87 | 18.67 |

O. 1-(5-Dimethylsulfamoyl-1,3,4-thiadiazol-2-yl)-1-ethyl-3-methylurea, having a melting point of about 152°–154° C., and weighing 5.1 g., from 6 g. of 2-ethylamino-1,3,4-thiadazole-5-(N,N-dimethyl)sulfonamide and 2.3 ml. of methylisocyanate.

Analyses calculated for $C_8H_{15}N_5O_3S_2$:

|   | Theoretical | Found |
|---|---|---|
| C | 32.75% | 32.74% |
| H | 5.15 | 4.91 |
| N | 23.87 | 23.72 |

P. 1-[5-[N-(2-Chloroethyl)-N-methylsulfamoyl]-1,3,4-thiadiazol-2-yl]-1-ethyl-3-methylurea, having a melting point of about 105°–107° C., and weighing 6.2 g., from 6.3 g. of 2-ethylamino-1,3,4-thiadiazole-5-[N-(2-chloroethyl)-N-methyl]sulfonamide and 1.9 ml. of methylisocyanate.

Analyses calculated for $C_9H_{16}N_5O_3S_2Cl$:

|   | Theoretical | Found |
|---|---|---|
| C | 31.62% | 31.60% |
| H | 4.71 | 4.95 |
| N | 20.49 | 20.47 |

Q. 1-[5-(Diethylsulfamoyl)-1,3,4-thiadiazol-2-yl]-1-ethyl-3-methylurea, having a melting point of about 127°–129° C., and weighing 1.9 g., from 3.9 g. of 2-ethylamino-1,3,4-thiadiazole-5-(N,N-diethyl)sulfonamide and 1 ml. of methylisocyanate.

Analyses calculated for $C_{10}H_{19}N_5O_3S_2$:

|   | Theoretical | Found |
|---|---|---|
| C | 37.37% | 37.26% |
| H | 5.96 | 5.71 |
| N | 21.79 | 21.76 |
| S | 19.95 | 19.98 |

R. 1-[5-[N-(s-Butyl)-N-methylsulfamoyl]-1,3,4-thiadiazol-2-yl]-1-ethyl-3-methylurea, having a melting point of about 114°-116° C., and weighing 1.33 g., from 4.8 g. of 2-ethylamino-1,3,4-thiadiazole-5-(N-s-butyl-N-methyl)sulfonamide and 1.1 ml. of methylisocyanate.

Analysis calculated for $C_{11}H_{21}N_5O_3S_2$:

|   | Theoretical | Found |
|---|---|---|
| C | 39.39% | 39.10% |
| H | 6.31 | 6.04 |
| N | 20.88 | 20.74 |
| S | 19.12 | 19.10 |

S. 1-[5-[N-(2,2-Dimethoxyethyl)-N-methylsulfamoyl]-1,3,4-thiadiazol-2-yl]-1-ethyl-3-methylurea, as an oil, and weighing 2.7 g., from 3.5 g. of 2-ethylamino-1,3,4-thiadiazole-5-[N-(2,2-dimethoxyethyl)-N-methyl]-sulfonamide and 0.75 ml. of methylisocyanate.

Analyses calculated for $C_{11}H_{21}N_5O_5S_2$:

|   | Theoretical | Found |
|---|---|---|
| C | 35.96% | 36.02% |
| H | 5.76 | 5.91 |
| N | 19.06 | 19.03 |
| S | 17.45 | 17.65 |

EXAMPLE 11

1-[5-[N-(2,2-Dimethoxyethyl)-N-methylsulfamoyl]-1,3,4-thiadiazol-2-yl]-1,3-dimethylurea A suspension was prepared of 3 g. of 1,3-dimethyl-3-(5-chlorosulfonyl-1,3,4-thiadiazol-2-yl)urea in 30 ml. of tetrahydrofuran, and to the suspension was slowly added 1.31 g. of methylaminoacetaldehyde dimethylacetal. After the addition was complete, there was added dropwise a solution of 1.11 g. of triethylamine in 8 ml. of tetrahydrofuran. During the additions, the reaction mixture was cooled in a cold water bath. The reaction mixture was then stirred overnight and was worked up by adding water. The precipitate which formed was filtered off and washed with water. The solid thus obtained had a melting point of about 149°-151° C., and weighed 2.3 g. It was identified by NMR spectrum and elemental analyses as 1-[5-[N-(2,2-dimethoxyethyl)-N-methylsulfamoyl]-1,3,4-thiadiazol-2-yl]-1,3-dimethylurea.

Analyses calculated for $C_{10}H_{19}N_5O_5S_2$:

|   | Theoretical | Found |
|---|---|---|
| C | 33.99% | 33.77% |
| H | 5.42 | 5.21 |
| N | 19.82 | 19.60 |

Following the same general procedure of Example 11, additional compounds were prepared. The compounds, together with the principal starting materials used in their synthesis and weights thereof, are set forth hereinafter. The compounds were identified as indicated.

A. 3-[5-(Diethylsulfamoyl)-1,3,4-thiadiazol-2-yl]-1,1-dimethylurea, having a melting point of about 166°-169° C., and weighing 1.8 g., from 4 g. of 1,1-dimethyl-3-(5-chlorosulfonyl-1,3,4-thiadiazol-2-yl)urea and 2 g. of diethylamine.

Analyses calculated for $C_9H_{17}N_5O_3S_2$:

|   | Theoretical | Found |
|---|---|---|
| C | 35.17% | 34.91% |
| H | 5.57 | 5.34 |
| N | 22.78 | 22.89 |
| S | 20.86 | 20.95 |

B. 1-Methyl-3-[5-(methyl-2-propynylsulfamoyl)-1,3,4-thiadiazol-2-yl]urea, having a melting point of about 177°-179° C., from 5 g. of 1-methyl-3-(5-chlorosulfonyl-1,3,4-thiadiazol-2-yl)urea and 5 g. of methyl-2-propynylamine.

Analyses calculated for $C_8H_{11}N_5O_3S_2$:

|   | Theoretical | Found |
|---|---|---|
| C | 33.21% | 33.46% |
| H | 3.83 | 3.66 |
| N | 24.21 | 23.98 |

C. 3-[5-(N-Isopropyl-N-methylsulfamoyl)-1,3,4-thiadiazol-2-yl]-1,1-dimethylurea, having a melting point of about 179°-181° C., and weighing 2.78 g., from 7 g. of 1,1-dimethyl-3-(5-chlorosulfonyl-1,3,4-thiadiazol-2-yl)urea and 2.1 g. of methylisopropylamine.

Analyses calculated for $C_9H_{17}N_5O_3S_2$:

|   | Theoretical | Found |
|---|---|---|
| C | 35.17% | 35.27% |
| H | 5.57 | 5.32 |
| N | 22.78 | 23.01 |
| S | 20.86 | 20.79 |

D. 3-[5-(N-Allyl-N-methylsulfamoyl)-1,3,4-thiadiazol-2-yl]-1,1-dimethylurea, having a melting point of about 137°-139° C., and weighing 2.8 g., from 8 g. of 1,1-dimethyl-3-(5-chlorosulfonyl-1,3,4-thiadiazol-2-yl)urea and 2.3 g. of N-allyl-N-methylamine.

Analyses calculated for $C_9H_{15}N_5O_3S_2$:

|   | Theoretical | Found |
|---|---|---|
| C | 35.40% | 35.67% |
| H | 4.95 | 4.72 |
| N | 22.93 | 23.16 |
| S | 21.00 | 21.06 |

E. 1-[5-[N-(2-Chloroethyl)-N-ethylsulfamoyl]-1,3,4-thiadiazol-2-yl]-1,3-dimethylurea, having a melting point of about 155°-157° C., and weighing 3.02 g., from 4 g. of 1,3-dimethyl-3-(5-chlorosulfonyl-1,3,4-thiadiazol-2-yl)urea and 2.01 g. of ethylaminoethyl chloride hydrochloride.

Analyses calculated for $C_9H_{16}ClN_5O_3S_2$:

|   | Theoretical | Found |
|---|---|---|
| C | 31.62% | 31.55% |
| H | 4.72 | 5.00 |
| N | 20.49 | 20.62 |

F. 1-[5-[N-(2-Chloroethyl)-N-methylsulfamoyl]-1,3,4-thiadiazol-2-yl]-3,3-dimethylurea, having a melting point of about 173°-175° C. and weighing 3.2 g., from 8 g. of 1,1-dimethyl-3-(5-chlorosulfonyl-1,3,4-thiadiazol-2-yl)urea and 5.2 g. of N-(2-chloroethyl)-N-methylamine hydrochloride. Identified by NMR spectrum and elemental analyses.

Analyses calculated for $C_8H_{14}N_5O_3S_2Cl$:

|   | Theoretical | Found |
|---|---|---|
| C | 29.31% | 29.07% |
| H | 4.30 | 4.19 |
| N | 21.36 | 21.35 |
| S | 19.56 | 19.60 |
| Cl | 10.82 | 11.20 |

EXAMPLE 12

1-[5-(N-Butyl-N-methylsulfamoyl)-1,3,4-thiadiazol-2-yl]-1,3,3-trimethylurea

Phosgene was bubbled into a well-stirred suspension of 15 g. of 2-methylamino-1,3,4-thiadiazole-5-(N-butyl-N-methyl)sulfonamide in 200 ml. of toluene at a temperature of about 100° C. A solid formed, and when it had dissolved, the phosgene was bubbled into the mixture for an additional 30 minutes. Nitrogen was then bubbled through the solution for about 1 hour. The mixture was filtered while hot and allowed to cool to about 25° C. Aqueous dimethylamine solution, 18 g., was then added slowly to the mixture, keeping the reaction temperature below 30° C. by cooling. When the addition was complete, the solution was heated at about 60° C. for about one-half hour. The reaction mixture was then cooled and was washed twice with 100 ml. portions of water and the water washings discarded. The toluene layer was concentrated in vacuo to yield a red oil. This red oil was chromatographed on a silica gel column using ethyl acetate as solvent and eluant. The solvent of the collected fractions was evaporated in vacuo to yield a clear oil weighing 9.6 g. The product was identified by NMR and IR spectra, and elemental analyses, as 1-[5-(N-butyl-N-methylsulfamoyl)-1,3,4-thiadiazol-2-yl]-1,3,3-trimethylurea.

Analyses calculated for $C_{11}H_{21}N_5O_3S_2$:

|   | Theoretical | Found |
|---|---|---|
| C | 39.39% | 39.68% |
| H | 6.31 | 6.20 |
| N | 20.88 | 20.58 |
| S | 19.12 | 19.40 |

EXAMPLE 13

1,1-Dimethyl-3-[5-(N-methyl-N-propylsulfamoyl)-1,3,4-thiadiazol-2-yl]urea

This compound was prepared stepwise.

Step 1.

A suspension was prepared of 10 g. of 2-amino-5-mercapto-1,3,4-thiadiazole, 12 ml. of concentrated aqueous hydrochloric acid, and 40 ml. of water. Chlorine was bubbled into this stirred suspension through sulfuric acid at a moderate rate while the temperature of the reaction mixture was held at about 5°-10° C., with external cooling. Green bubbles developed on top of the mixture and the mixture turned rust brown and yellow in color. Vigorous stirring was continued while the chlorine was bubbled into the suspension until saturation was achieved. The reaction product mixture was then filtered and the solid material washed well with water. There was obtained 5 g. of product having a melting point of about 135°-137° C., and identified as 2-amino-5-chlorosulfonyl-1,3,4-thiadiazole. The reaction was repeated a number of times in order to build up a supply of the starting material.

Step 2.

To a suspension of 7 g. of 2-amino-5-chlorosulfonyl-1,3,4-thiadiazole in 30 ml. of tetrahydrofuran, there was slowly added 3.0 g. of N-methyl-n-propylamine. The suspension cleared. With continued cooling of the solution in an ice bath, there was slowly added a solution of 4.2 g. of triethylamine in a few milliliters of tetrahydrofuran. A precipitate separated. The reaction mixture was stirred overnight at ambient room temperature. The reaction product mixture was worked up by pouring it onto crushed ice. The precipitate which separated was filtered off and washed with water and dried. There was obtained 5.0 g. of product having a melting point of about 137°-140° C. The product was identified as 2-amino-1,3,4-thiadiazole-5-(N-methyl-N-propyl)sulfonamide.

Step 3.

A suspension was prepared of 5 g. of 2-amino-1,3,4-thiadiazole-5-(N-methyl-N-propyl)sulfonamide in 60 ml. of toluene, and to the suspension there was added dropwise a solution of 3.6 g. of phenylchloroformate in 10 ml. of toluene. The reaction mixture was refluxed for about 3 hours, at which time complete solution had occurred. The reaction product mixture was allowed to cool overnight, and was filtered to recover the material which had precipitated. The material collected on the funnel was washed with hexane and dried. The product weighed 6.5 g. and had a melting point of about 157°-160° C. The product was identified as 5-[(N-methyl-N-propyl)sulfamoyl-1,3,4-thiadiazol-2-yl]carbamic acid, phenyl ester. It was used as is without further purification in the final step of the synthesis.

Step 4.

A suspension was prepared of 6.5 g. of the carbamic acid, phenyl ester, prepared above, in 50 ml. of benzene, and to the suspension there was slowly added 1.5 g. of dimethylamine hydrochloride. After the addition was complete, there was slowly added a solution of 2.0 g. of triethylamine in a few milliliters of benzene. The suspension dissolved and complete solution occurred in the reaction mixture. The reaction mixture was refluxed for about 5.5 hours, during which time a precipitate separated. The reaction mixture was cooled and filtered and the filtrate was concentrated in vacuo, leaving a residue. The residue was removed from the filter flask with a minimum amount of cold benzene and the residue was recrystallized from commercial absolute ethanol. There was obtained 3.5 g. of product having a melting point of about 159°-161° C. The product was identified by NMR spectrum and elemental analyses as 1,1-dimethyl-3-[5-(N-methyl-N-propylsulfamoyl)-1,3,4-thiadiazol-2-yl]urea.

Analyses calculated for $C_9H_{17}N_5O_3S_2$:

|   | Theoretical | Found |
|---|---|---|
| C | 35.17% | 35.33% |
| H | 5.57 | 5.68 |
| N | 22.78 | 22.59 |
| S | 20.86 | 21.14 |

Following the same general procedure outlined in Example 13, an additional compound was prepared. The principal reactants and the weights thereof are set forth hereinbelow.

A. 3-[5-(N-Ethyl-N-methylsulfamoyl)-1,3,4-thiadiazol-2-yl]-1,1-dimethylurea

This compound was also prepared stepwise.

Step 1.

2-Amino-1,3,4-thiadiazole-5-(N-ethyl-N-methyl)sulfonamide, having a melting point of about 124°-127° C., and weighing 3.2 g., from 7.4 g. of 2-amino-5-chlorosulfonyl-1,3,4-thiadiazole and 2.36 g. of ethylmethylamine.

Step 2.

5-[(N-Ethyl-N-methyl)sulfamoyl-1,3,4-thiadiazol-2-yl]carbamic acid, phenyl ester, having a melting point of about 187°-197° C., and weighing 4 g., from 3.2 g. of 2-amino-1,3,4-thiadiazole-5-(N-ethyl-N-methyl)sulfonamide and 1.2 g. of phenylchloroformate. The material was used without further purification.

Step 3.

3-[5-(N-methylsulfamoyl)-1,3,4-thiadiazol-2-yl]-1,1-dimethylurea, from 4 g. of the carbamic acid, phenyl ester, above, and 3 g. of diethylamine hydrochloride. The product had a melting point of about 152°-153° C. and weighed 1.5 g.

Analyses calculated for $C_8H_{15}N_5O_3S_2$:

|   | Theoretical | Found |
|---|---|---|
| C | 32.75% | 32.84% |
| H | 5.15 | 4.87 |
| N | 23.87 | 23.62 |
| S | 21.86 | 22.18 |

The compounds of generic formula (I) wherein $R^4$ is hydrogen, form metal and ammonium salts (substituted or unsubstituted). For polyvalent metals, the salt compounds are chelate in character. The alkali metal and ammonium salts provide highly desirable properties such as water solubility when employed for use in agricultural applications. Preparation of these salts is described in U.S. Pat. No. 3,565,901 (Feb. 23, 1971), which description is hereby incorporated herein and made a part of this disclosure.

The preparations of the salts of compounds wherein $R^4$=H are described in the examples which follow.

EXAMPLE 14

3-[5-(Dimethylsulfamoyl)-1,3,4-thiadiazol-2-yl]-1,1-dimethylurea, potassium salt To a solution of 1.5 g. of 3-[5-(dimethylsulfamoyl)-1,3,4-thiadiazol-2-yl]-1,1-dimethylurea in 15 ml. of methanol, there was added 15 ml. of a saturated methanolic solution of potassium hydroxide. The reaction mixture was stirred for a time and was then filtered. The precipitate was collected, washed with ether, and air dried. It weighed 1.1 g., and had a melting point of about 322°-325° C. This product was identified by NMR spectrum and elemental analyses as 3-[5-(dimethylsulfamoyl)-1,3,4-thiadiazol-2-yl]-1,1-dimethylurea, potassium salt.

Analyses calculated for $C_7H_{12}N_5O_3S_2K$:

|   | Theoretical | Found |
|---|---|---|
| C | 26.49% | 26.46% |
| H | 3.81 | 3.54 |
| N | 22.06 | 21.83 |

Following the same general procedure as used in Example 14, additional salts were prepared. The principal starting materials and the amounts thereof are set forth in the examples which appear hereinafter.

A. 1-[5-[N-(2-Chloroethyl)-N-methylsulfamoyl]-1,3,4-thiadiazol-2-yl]-3-methylurea, potassium salt, having a melting point of about 147°-150° C., and weighing 1.1 g., from 5 g. of 1-[5-[N-(2-chloroethyl)-N-methylsulfamoyl]-1,3,4-thiadiazol-2-yl]-3-methylurea and saturated methanolic potassium hydroxide solution.

Analyses calculated for $C_8H_{15}N_5O_4S_2ClK$:

|   | Theoretical | Found |
|---|---|---|
| C | 25.03% | 24.92% |
| H | 3.94 | 3.79 |
| N | 18.24 | 17.94 |

B. 1-[5-(N-Ethyl-N-methylsulfamoyl)-1,3,4-thiadiazol-2-yl]-3-methylurea, potassium salt, having a melting point of about 149°-151° C., and weighing 1 g., from 5 g. of 1-[5-(N-ethyl-N-methylsulfamoyl)-1,3,4-thiadiazol-2-yl]-3-methylurea and 25 ml. of a saturated methanolic potassium hydroxide solution.

Analyses calculated for $C_8H_{16}N_5O_4S_2K$:

|   | Theoretical | Found |
|---|---|---|
| C | 27.49% | 27.20% |
| H | 4.61 | 4.35 |
| N | 20.04 | 19.99 |

C. 3-[5-[N-(2-Chloroethyl)-N-methylsulfamoyl]-1,3,4-thiadiazol-2-yl]-1,1-dimethylurea, potassium salt, having a melting point of about 220°-221° C., and weighing 620 mg., from 750 mg. of 3-[5-[N-(2-chloroethyl)-N-methylsulfamoyl]-1,3,4-thiadiazol-2-yl]-1,1-dimethylurea and 10 ml. of saturated methanolic potassium hydroxide solution.

Analyses calculated for $C_8H_{13}N_5O_3S_2ClK$:

|   | Theoretical | Found |
|---|---|---|
| C | 26.26% | 26.05 |
| H | 3.58 | 3.47 |
| N | 19.14 | 18.86 |

D. 3-[5-(N-Ethyl-N-methylsulfamoyl)-1,3,4-thiadiazol-2-yl]-1,1-dimethylurea, potassium salt, having a melting point of about 282°-284° C., and weighing 1.9 g., from 3 g. of 3-[5-(N-ethyl-N-methylsulfamoyl)-1,3,4-thiadiazol-2-yl]-1,1-dimethylurea and 25 ml. of saturated methanolic potassium hydroxide solution.

Analyses calculated for $C_8H_{14}N_5O_3S_2K$:

|   | Theoretical | Found |
|---|---|---|
| C | 28.99% | 28.71% |
| H | 4.26 | 4.07 |
| N | 21.13 | 21.01 |

E. 3-[5-(Diethylsulfamoyl)-1,3,4-thiadiazol-2-yl]-1,1-dimethylurea, potassium salt, having a melting point of about 287°–288° C., and weighing 2.7 g., from 3 g. of 3-[5-(diethylsulfamoyl)-1,3,4-thiadiazol-2-yl]-1,1-dimethylurea and 25 ml. of saturated methanolic potassium hydroxide solution.

Analyses calculated for $C_9H_{16}N_5O_3S_2K$:

|   | Theoretical | Found |
|---|---|---|
| C | 31.29% | 31.50% |
| H | 4.67 | 4.56 |
| N | 20.27 | 20.28 |

Compounds possessing the structures of generic formula (I) may be used in the herbicidal method of the present invention. The compounds may be used in various states of purity, ranging, for example, from crystals to a technical crude grade. Suitable solvents for these compounds include alcohols, aqueous alcohol solutions, and ketones, including acetone and methyl isobutyl ketone.

Each compound to be used in the herbicidal method of this invention may be prepared as a simple solution in an appropriate solvent in which the compound is completely soluble at the desired concentration. Appropriate solvents include water, alcohols, acetone, aqueous alcohol and acetone, and other organic solvents. These simple solutions may be further modified by the addition of various surfactants, emulsifying or dispersing agents, colorants, odorants, antifoaming agents, other herbicides or herbicidal oils which supplement or synergize the activity of the herbicides used in the invention, or other adjuvants for any given application where deemed desirable. Compounds usable in the herbicidal method of the invention may also be formulated in various other types of formulations commonly recognized by those skilled in the art of agricultural chemicals. These formulations include, for example, compositions containing the active ingredient as granules of relatively large particle size, as powder dusts, as wettable powders, as emulsifiable concentrates, or as a constituent part of any other known type of formulation commonly utilized by those skilled in the art. Such formulations include the adjuvants and carriers normally employed for facilitating the dispersion of active ingredients for agricultural and industrial applications of phytotoxicants. These formulations may contain as little as 0.25 percent or as much as 95 percent or more by weight of the active ingredient.

Dust formulations are prepared by mixing the active thiadiazole ingredient with finely-divided pulverulent solids which act as dispersants and carriers for the phytotoxicant in applying it to the locus of application for vegetation control. Typical solids which may be utilized in preparing dust formulations of the active ingredients of the invention include talc, hydrated sodium silico aluminates, hydrated silicon dioxide, kieselguhr, finely-divided clay, fullers' earth, or other common organic or inorganic solids. Solids utilized in preparing dust formulations of the active ingredient normally have a particle size of 50 microns or less. The active ingredient of these dust formulations is present commonly in as little as 0.25 percent to as much as 30 percent or more by weight of the composition.

Granular formulations of the active ingredients are prepared by impregnating or adsorbing the toxicant on or into relatively coarse particles of inert solids such as sand, attapulgite clay, gypsum, corn cobs or other inorganic or organic solids. The active ingredient of these granular formulations is commonly present in from about 1 percent to as much as 20 percent or more by weight of the composition.

Wettable powder formulations are solid compositions of matter wherein the active ingredient is absorbed or adsorbed in or on a sorptive carrier such as finely-divided clay, talc, gypsum, lime, wood flour, fullers' earth, kieselguhr, or the like. These formulations preferably are made to contain from about 50 percent to about 80 percent of active ingredient. These wettable powder formulations commonly contain a small amount of a wetting, dispersing, or emulsifying agent to facilitate dispersion in water or other liquid carrier utilized to distribute the phytotoxicant to the locus of desired vegetation control. Suitable surfactants, emulsifying agents, and dispersants include both anionic and nonionic substances such as alkyl ether sodium sulfate and alkyl aryl polyethoxyethanols, sodium N-methyl-N-palmitoyltaurate, the oleic acid ester of sodium isethionate, sodium lignosulfonate, alkyl aryl sulfonates, highly polymerized naphthalenesulfonate, alkyl aryl polyether alcohols, sodium lauryl sulfate, and the like.

Emulsifiable concentrate formulations are homogeneous liquid or paste compositions containing the active ingredient. Such compositions will disperse in water or other liquid carrier to facilitate application of the phytotoxicant to the locus of desired vegetation control. Such emulsifiable concentrate formulations of the active ingredients may contain only the active ingredient with a liquid or solid emulsifying agent, or may contain other relatively nonvolatile organic solvents such as isophorane, dioxane, heavy aromatic napthas, xylene, or dimethylformamide. The active ingredient in such formulations commonly comprises from about 10 percent to about 70 percent by weight of the phytotoxicant composition.

The novel process of this invention comprises treating a soil area or locus wherein wheat has been grown and harvested with a compound of the formula set forth hereinabove. Thus, the herbicidally-active compound or compositions containing the herbicidally-active compound are sprayed, dusted, or spread by other methods well known to the art onto the particular area at the rate of from about 0.56 to about 4.5 kilograms per hectare. For most field applications, it is preferred to spray the herbicidal composition at the rate of from about 0.56 to about 1.1 kg. of active ingredient per hectare.

Representative compounds coming within the scope of generic formula (I), supra, have been evaluated for their preemergent herbicidal properties against seven plant species, as described in the following greenhouse experiments.

EXPERIMENT 1

A soil was prepared consisting of 1 part masonry sand and 1 part shredded topsoil blended together. Galvanized flats, measuring 21.5 by 31.5 by 8 cm., were filled with 3.785 liters of this soil mixture and the soil patted down with a bench brush until level. The seeds were planted in rows perpendicular to the long axis of the flat, one species per row. The seven plant species used, numbered consecutively for identification purposes in Chart 1, and the approximate number of seeds planted, were as follows:

1. wheat (*Triticum aestivum*) 40
2. sorghum (*Sorghum vulgari*) 12
3. wild oat (*Avena fatua*) 25
4. foxtail millet (*Setaria italica*) 100
5. pigweed (*Amaranthus retroflexus*) 350
6. mustard (Brassica sp.) 125
7. lambsquarter (*Chenopodium album*) 100

After planting, the seeds were covered with 0.5 to 1.0 cm. of screened soil.

The compounds were formulated for the tests as follows:

Each compound was dissolved in acetone and ethanol (1:1 ratio) containing a small amount of a mixture of surfactants (Toximul R and Toximul S). Toximul R and Toximul S are each a sulfonate/nonionic blend available from Stepan Chemical Company, Northfield, Illinois. The volume of solvent was 10 percent of the final spray volume. The solution was then diluted with deionized water to 25 ml. (solution A).

Using a modified DeVilbiss atomizer hooked to an air source, 12.5 ml. of this solution (solution A) was sprayed on a test flat to provide an application rate of 4.5 kg./ha. The remaining 12.5 ml. of solution A was diluted to a volume of 25 ml., using deionized water containing a small amount of Toximul R and Toximul S, to form solution B. Solution B, 12.5 ml., was sprayed on each test flat to provide an application rate of 2.2 kg./ha. The remaining 12.5 ml. of solution B was diluted to 25 ml., again with deionized water containing Toximul R and Toximul S, to form solution C. Application of 12.5 ml. of solution C per flat provided test compound at the rate of 1.1 kg./ha. The remaining 12.5 ml. of solution C was diluted to 25 ml. using deionized water containing Toximul R and Toximul S, and 12.5 ml. of the solution thus obtained (solution D) was applied to test flats to give an application rate of 0.56 kg./ha. These applications all were made on the day of planting or the succeeding day. The flats were then placed in the greenhouse.

Injury ratings, as percent control, were made by observations made 17 to 21 days after treatment. The injury rating scale was 0–100, where 0=no control, and 100=100 percent control.

All of the test compounds used in the various greenhouse tests and field trials described herein are each identified by a number, and are recorded here in the following list:

1. 1-[5-[N-(2-Chloroethyl)-N-methylsulfamoyl]-1,3,4-thiadiazol-2-yl]-1-ethyl-3-methylurea
2. 1-[5-[N-(2,2-Dimethoxyethyl)-N-methylsulfamoyl]-1,3,4-thiadiazol-2-yl]-1,3-dimethylurea
3. 1,3-Dimethyl-1-(5-methylsulfonyl-1,3,4-thiadiazol-2-yl)urea
4. 1-(5-Ethylthio-1,3,4-thiadiazol-2-yl)-1,3-dimethylurea
5. 1-(5-Ethylsulfonyl-1,3,4-thiadiazol-2-yl)-1,3-dimethylurea
6. 1-[5-(s-Butylsulfonyl)-1,3,4-thiadiazol-2-yl]-1,3-dimethylurea
7. 1-(5-Dimethylsulfamoyl-1,3,4-thiadiazol-2-yl)-1,3-dimethylurea
8. 1-[5-[N-(2-Chloroethyl)-N-methylsulfamoyl]-1,3,4-thiadiazol-2-yl]-1,3,3-trimethylurea
9. 1-[5-[N-(2,2-Dimethoxyethyl)-N-methylsulfamoyl]-1,3,4-thiadiazol-2-yl]-1,3,3-trimethylurea
10. 1-[5-(N-Methoxy-N-methylsulfamoyl)-1,3,4-thiadiazol-2-yl]-1,3,3-trimethylurea
11. 1,1,3-Trimethyl-3-[5-[N-(s-butyl)-N-methylsulfamoyl]-1,3,4-thiadiazol-2-yl]urea
12. 1-(5-Dimethylsulfamoyl-1,3,4-thiadiazol-2-yl)-1-ethyl-3-methylurea
13. 1-[5-(N-Ethyl-N-methylsulfamoyl)-1,3,4-thiadiazol-2-yl]-1,3-dimethylurea
14. 1-(5-Dimethylsulfamoyl-1,3,4-thiadiazol-2-yl)-3-methylurea
15. 1,3-Dimethyl-1-(5-propylsulfonyl-1,3,4-thiadiazol-2-yl)urea
16. 1-[5-[N-(2-Chloroethyl)-N-methylsulfamoyl]-1,3,4-thiadiazol-2-yl]-1,3-dimethylurea
17. 1,3-Dimethyl-1-[5-(N-methyl-N-propylsulfamoyl)-1,3,4-thiadiazol-2-yl]urea
18. 1,1-Dimethyl-3-[5-(methylsulfonyl)-1,3,4-thiadiazol-2-yl]urea
19. 3-[5-(Dimethylsulfamoyl)-1,3,4-thiadiazol-2-yl]-1,1-dimethylurea, potassium salt
20. 1-[5-(N-Ethyl-N-methylsulfamoyl)-1,3,4-thiadiazol-2-yl]-1,3,3-trimethylurea
21. 1-[5-(Diethylsulfamoyl)-1,3,4-thiadiazol-2-yl]-1,3-dimethylurea
22. 1-[5-(N-Ethyl-N-methylsulfamoyl)-1,3,4-thiadiazol-2-yl]-3-methylurea, potassium salt
23. 1-[5-(N-Allyl-N-methylsulfamoyl)-1,3,4-thiadiazol-2-yl]-3,3-dimethylurea
24. 1-[5-[N-Methyl-N-(2-propynyl)sulfamoyl]-1,3,4-thiadiazol-2-yl]-1,3-dimethylurea
25. 1-[5-(N-Butyl-N-methylsulfamoyl)-1,3,4-thiadiazol-2-yl]-1,3,3-trimethylurea
26. 1-[5-(N-Isobutyl-N-methylsulfamoyl)-1,3,4-thiadiazol-2-yl]-1,3,3-trimethylurea
27. 1-[5-[N-(2-Chloroethyl)-N-methylsulfamoyl]-1,3,4-thiadiazol-2-yl]-3,3-dimethylurea
28. 1-[5-(N-Ethyl-N-methylsulfamoyl)-1,3,4-thiadiazol-2-yl]-3,3-dimethylurea
29. 3-[5-(Diethylsulfamoyl)-1,3,4-thiadiazol-2-yl]-1,1-dimethylurea
30. 3-[5-[N-(2-Chloroethyl)-N-methylsulfamoyl]-1,3,4-thiadiazol-2-yl]-1,1-dimethylurea, potassium salt
31. 3-[5-(N-Ethyl-N-methylsulfamoyl)-1,3,4-thiadiazol-2-yl]-1,1-dimethylurea, potassium salt
32. 3-[5-(Diethylsulfamoyl)-1,3,4-thiadiazol-2-yl]-1,1-dimethylurea, potassium salt
33. 1-[5-(N-Methyl-N-propylsulfamoyl)-1,3,4-thiadiazol-2-yl]-3,3-dimethylurea
34. 1-[5-(N-Ethyl-N-methylsulfamoyl)-1,3,4-thiadiazol-2-yl]-1-ethyl-3-methylurea
35. 1-[5-(N-Methyl-N-propylsulfamoyl)-1,3,4-thiadiazol-2-yl]-1-ethyl-3-methylurea
36. 1-[5-(N-Isobutyl-N-methylsulfamoyl)-1,3,4-thiadiazol-2-yl]-1-ethyl-3-methylurea
37. 1-[5-(N-Allyl-N-methylsulfamoyl)-1,3,4-thiadiazol-2-yl]-1-ethyl-3-methylurea The results of this experiment are set forth in Chart 1, which follows. In the chart, column 1 identifies the compound under test; column 2, the rate in kg./ha. at which the compound was applied to the test flat; and the remaining columns, the percent control for the particular plant species.

Chart 1

Percent Control Preemergence Test

| Compound No. | Appln. Rate kg./ha. | wheat | sorghum | wild oat | foxtail millet | pigweed | mustard | lambs-quarter |
|---|---|---|---|---|---|---|---|---|
| 1 | 0.56 | 60 | 40 | 90 | 80 | 100 | 100 | 100 |
|   | 1.1 | 100 | 80 | 100 | 100 | 100 | 100 | 100 |
|   | 2.2 | 100 | 90 | 100 | 100 | 100 | 100 | 100 |
|   | 4.5 | 100 | 90 | 100 | 100 | 100 | 100 | 100 |
| 2 | 0.56 | 70 | 40 | 100 | 80 | 100 | 100 | 100 |
|   | 1.1 | 100 | 100 | 100 | 100 | 100 | 100 | 100 |
|   | 2.2 | 100 | 100 | 100 | 100 | 100 | 100 | 100 |
|   | 4.5 | 100 | 100 | 100 | 100 | 100 | 100 | 100 |
| 3 | 0.56 | 90 | 70 | 90 | 90 | 100 | 100 | 100 |
|   | 1.1 | 100 | 100 | 100 | 100 | 100 | 100 | 100 |
|   | 2.2 | 100 | 100 | 100 | 100 | 100 | 100 | 100 |
|   | 4.5 | 100 | 100 | 100 | 100 | 100 | 100 | 100 |
| 4 | 0.56 | 60 | 50 | 70 | 70 | 100 | 80 | 100 |
|   | 1.1 | 80 | 60 | 100 | 90 | 100 | 100 | 100 |
|   | 2.2 | 100 | 90 | 100 | 100 | 100 | 100 | 100 |
|   | 4.5 | 100 | 100 | 100 | 100 | 100 | 100 | 100 |
| 5 | 0.56 | 100 | 80 | 100 | 100 | 100 | 100 | 100 |
|   | 1.1 | 100 | 90 | 100 | 100 | 100 | 100 | 100 |
|   | 2.2 | 100 | 100 | 100 | 100 | 100 | 100 | 100 |
|   | 4.5 | 100 | 100 | 100 | 100 | 100 | 100 | 100 |
| 6 | 0.56 | 50 | 40 | 80 | 80 | 100 | 100 | 100 |
|   | 1.1 | 80 | 80 | 100 | 100 | 100 | 100 | 100 |
|   | 2.2 | 100 | 100 | 100 | 100 | 100 | 100 | 100 |
|   | 4.5 | 100 | 100 | 100 | 100 | 100 | 100 | 100 |
| 7 | 0.56 | 70 | 70 | 100 | 90 | 70 | 100 | 100 |
|   | 1.1 | 100 | 90 | 100 | 100 | 100 | 100 | 100 |
|   | 2.2 | 100 | 100 | 100 | 100 | 100 | 100 | 100 |
|   | 4.5 | 100 | 100 | 100 | 100 | 100 | 100 | 100 |
| 8 | 0.56 | 80 | 80 | 90 | 100 | 90 | 100 | 100 |
|   | 1.1 | 100 | 100 | 100 | 100 | 100 | 100 | 100 |
|   | 2.2 | 100 | 100 | 100 | 100 | 100 | 100 | 100 |
|   | 4.5 | 100 | 100 | 100 | 100 | 100 | 100 | 100 |
| 9 | 0.56 | 70 | 60 | 100 | 90 | 100 | 100 | 100 |
|   | 1.1 | 100 | 80 | 100 | 100 | 100 | 100 | 100 |
|   | 2.2 | 100 | 90 | 100 | 100 | 100 | 100 | 100 |
|   | 4.5 | 100 | 100 | 100 | 100 | 100 | 100 | 100 |
| 10 | 0.56 | 70 | 20 | 70 | 80 | 100 | 100 | 100 |
|    | 1.1 | 100 | 70 | 100 | 90 | 100 | 100 | 100 |
|    | 2.2 | 100 | 90 | 100 | 100 | 100 | 100 | 100 |
|    | 4.5 | 100 | 100 | 100 | 100 | 100 | 100 | 100 |
| 11 | 0.56 | 70 | 30 | 40 | 80 | 100 | 100 | 100 |
|    | 1.1 | 100 | 80 | 100 | 100 | 100 | 100 | 100 |
|    | 2.2 | 100 | 100 | 100 | 100 | 100 | 100 | 100 |
|    | 4.5 | 100 | 100 | 100 | 100 | 100 | 100 | 100 |
| 12 | 0.56 | 100 | 90 | 100 | 100 | 100 | 100 | 100 |
|    | 1.1 | 100 | 100 | 100 | 100 | 100 | 100 | 100 |
|    | 2.2 | 100 | 100 | 100 | 100 | 100 | 100 | 100 |
|    | 4.5 | 100 | 100 | 100 | 100 | 100 | 100 | 100 |

EXPERIMENT 2

At the conclusion of the herbicidal study described in Experiment 1, the apparent X and 2X rates of application for each of the compounds were decided from the data provided by Experiment 1. The X rate of a compound was arbitrarily set as that rate which provided 90-100 percent control of all the plant species in the test. The present study was then conducted to determine the rate of degradation and the residual activity, that is, the persistence, of the test compounds by bioassaying the soil used in Experiment 1. The procedure was as follows.

The soil from each flat used in Experiment 1 was thoroughly mixed and fortified with dextrose (10% by weight) and yeast extract (0.2% by weight). This soil was then divided equally among four one-quart containers, three of which containers were stored in the greenhouse and the soil in the containers was maintained in a moist condition, but below field capacity. The soil in the fourth container was used in the first assay. The soil in this container was thoroughly mixed and equally divided between two four-inch square pots. One of these four-inch pots was seeded with grain sorghum (approximately 15 seeds), and the other 4-inch pot was seeded with wheat and mustard, one row of each, the seeding being done 34 days after the soil was originally treated in Experiment 1. The untreated soil in the control flats from Experiment 1 was utilized in the same manner to provide control readings of seeds planted and grown therein.

The pots of the first bioassay were observed on day 57 after original treatment to determine the percent control by the test compounds. The results are recorded in Chart 2, which follows hereinafter.

Using the soil from one of the containers which had been stored in the greenhouse as described above, a second bioassay was conducted in the same manner as described for the first bioassay. In this bioassay, the seeds of wheat, mustard and sorghum were planted 85 days after the soil was originally treated in Experiment 1. The pots in this second bioassay were observed on day 106 after the original treatment to determine the percent control by the test compounds, and the results are recorded in Chart 2, which follows.

A third bioassay was run using the soil from another of the containers of soil which had been stored in the greenhouse. The seeds of wheat, mustard and sorghum were planted 155 days after the soil was originally treated in Experiment 1. The pots in this third bioassay were observed on day 176 after original treatment, to determine the percent control by the test compounds. The results are recorded in Chart 2, hereinafter.

A fourth bioassay was run in the same manner using the last pot of soil which had been stored in the greenhouse. The seeds of wheat, mustard, and sorghum were planted in the pots on day 211 after the original treatment of the soil with the test compounds. The pots of this bioassay were observed on day 232 after original treatment to determine the percent control by the test compounds. The results are recorded in Chart 2, hereinafter.

In the chart, column 1 identifies the compound in the same manner as in Experiment 1; column 2 gives the original application rate of the test compounds in kg./ha. as applied in Experiment 1; columns 3, 8 and 13 give the percent control observed at the end of Experiment 1 for the particular plant species; the remaining columns give the percent control (at the indicated days after original treatment of the soil with the test compounds) for wheat, mustard and sorghum.

Chart 2

Percent Control

| Com- | | Wheat | | | | | Mustard | | | | | Sorghum | | | | |
|---|---|---|---|---|---|---|---|---|---|---|---|---|---|---|---|---|
| pound | kg./ha. | 0 | 57 | 106 | 176 | 232 | 0 | 57 | 106 | 176 | 232 | 0 | 57 | 106 | 176 | 232 |
| 1 | 1.1 | 95 | 85 | 40 | 90 | 30 | 100 | 80 | 100 | 100 | 30 | 85 | 60 | 40 | 10 | 10 |
|   | 2.2 | 100 | 100 | 50 | 90 | 90 | 100 | 100 | 100 | 100 | 100 | 90 | 90 | 60 | 30 | 30 |
| 2 | 1.1 | 98 | 100 | 30 | 60 | 40 | 100 | 100 | 100 | 98 | 80 | 95 | 40 | 20 | 40 | 30 |
|   | 2.2 | 98 | 100 | 50 | 98 | 80 | 100 | 100 | 00 | 100 | 100 | 98 | 85 | 60 | 40 | 40 |
| 3 | 0.56 | 90 | 70 | 30 | 50 | 40 | 100 | 98 | 80 | 70 | 20 | 70 | 40 | 30 | 0 | 0 |
|   | 1.1 | 95 | 100 | 60 | 100 | 98 | 100 | 100 | 80 | 100 | 100 | 95 | 65 | 50 | 50 | 50 |
| 4 | 1.1 | 80 | 80 | 30 | 99 | 99 | 100 | 100 | 100 | 100 | 100 | 60 | 70 | 60 | 70 | 60 |
|   | 2.2 | 95 | 100 | 60 | 100 | 100 | 100 | 100 | 100 | 100 | 100 | 92 | 95 | 80 | 95 | 90 |
| 5 | 1.1 | 95 | 100 | 50 | 95 | 98 | 100 | 100 | 100 | 100 | 100 | 92 | 98 | 80 | 70 | 70 |
|   | 2.2 | 98 | 100 | 60 | 100 | 100 | 100 | 100 | 100 | 100 | 100 | 85 | 98 | 100 | 90 | 98 |
| 6 | 1.1 | 80 | 60 | 10 | 0 | 50 | 100 | 00 | 100 | 100 | 100 | 80 | 65 | 40 | 30 | 50 |
|   | 2.2 | 98 | 100 | 20 | 90 | 90 | 100 | 100 | 100 | 100 | 100 | 95 | 98 | 70 | 50 | 60 |
| 7 | 1.1 | 98 | 90 | 10 | 40 | 60 | 99 | 100 | 100 | 50 | 50 | 92 | 50 | 20 | 10 | 0 |
|   | 2.2 | 98 | 100 | 40 | 90 | 90 | 100 | 100 | 100 | 100 | 100 | 95 | 95 | 60 | 40 | 30 |
| 8 | 1.1 | 95 | 50 | 0 | 30 | 30 | 100 | 100 | 100 | 100 | 95 | 95 | 45 | 30 | 40 | 10 |
|   | 2.2 | 98 | 100 | 20 | 80 | 50 | 100 | 100 | 100 | 100 | 100 | 95 | 70 | 50 | 50 | 30 |
| 9 | 1.1 | 98 | 85 | 20 | 50 | 20 | 100 | 100 | 100 | 80 | 30 | 80 | 25 | 20 | 10 | 0 |
|   | 2.2 | 98 | 100 | 50 | 90 | 70 | 100 | 100 | 100 | 100 | 100 | 92 | 90 | 60 | 30 | 0 |
| 10 | 2.2 | 100 | 100 | 60 | 80 | 70 | 100 | 100 | 100 | 100 | 100 | 90 | 80 | 50 | 60 | 40 |
|   | 4.5 | 100 | 100 | 80 | 100 | 80 | 100 | 100 | 100 | 100 | 100 | 95 | 100 | 70 | 80 | 55 |
| 11 | 2.2 | 95 | 80 | 40 | 70 | 85 | 100 | 100 | 50 | 100 | 100 | 95 | 40 | 40 | 10 | 10 |
|   | 4.5 | 98 | 100 | 60 | 100 | 100 | 100 | 100 | 100 | 100 | 100 | 98 | 85 | 50 | 50 | 50 |
| 12 | 0.56 | 98 | 90 | 40 | 40 | 50 | 100 | 100 | 100 | 60 | 40 | 90 | 50 | 40 | 20 | 10 |
|   | 1.1 | 100 | 100 | 60 | 98 | 80 | 100 | 100 | 100 | 100 | 100 | 98 | 85 | 60 | 50 | 50 |
| Control | 0 | 0 | 0 | 0 | 0 | 0 | 0 | 0 | 0 | 0 | 0 | 0 | 0 | 0 | 0 | 0 |

EXPERIMENT 3

The herbicidal activity of some of the compounds is further demonstrated by this greenhouse experiment wherein the compounds were again evaluated as preemergence herbicides against the same seven plant species used in Experiment 1 above.

The soil used in the experiment was prepared in the same manner as previously described in Experiment 1 and the whole experiment was carried out in the same way. The compounds were formulated in the same manner and applied by the same means.

Observations were made about 17 to 21 days after treatment and the percent control observed was based on a 0 to 100 scale where 0=no injury and 100 equals death of the plant, that is, 100 percent control.

The results obtained in the above experiment are set forth in Chart 3, which follows. In the chart, column 1 identifies the compound under test; column 2, the rate in kilograms per hectare (kg./ha.) at which the compound was applied to the test flat; and the remaining columns the percent control for the particular plant species.

Chart 3

Percent Control
Preemergence Test

| Compound | kg./ha. | Wheat | Sorghum | Wild Oat | Foxtail | Mustard | Pigweed |
|---|---|---|---|---|---|---|---|
| 1 | 1.1 | 100 | 90 | 100 | 98 | 98 | 98 |
|   | 2.2 | 99 | 80 | 100 | 100 | 100 | 99 |
| 5 | 0.56 | 99 | 99 | 100 | 100 | 100 | 99 |
|   | 1.1 | 100 | 99 | 100 | 100 | 100 | 100 |
| 7 | 0.56 | 99 | 100 | 95 | 100 | 98 | 100 |
|   | 1.1 | 100 | 100 | 100 | 100 | 100 | 100 |
|   | 2.2 | 100 | 100 | 100 | 100 | 100 | 100 |
| 12 | 0.56 | 100 | 95 | 100 | 98 | 100 | 98 |
|   | 1.1 | 100 | 100 | 100 | 100 | 100 | 100 |
|   | 2.2 | 100 | 99 | 100 | 100 | 100 | 100 |
| 13 | 0.56 | 100 | 99 | 100 | 100 | 100 | 99 |
|   | 1.1 | 100 | 100 | 100 | 100 | 100 | 100 |

-continued

Chart 3
Percent Control
Preemergence Test

| Compound | kg./ha. | Wheat | Sorghum | Wild Oat | Foxtail | Mustard | Pigweed |
|---|---|---|---|---|---|---|---|
|  | 2.2 | 100 | 100 | 100 | 100 | 100 | 100 |
| 14 | 1.1 | 100 | 80 | 70 | 100 | 100 | 100 |
|  | 2.2 | 99 | 100 | 100 | 100 | 100 | 99 |
| 15 | 1.1 | 100 | 100 | 100 | 100 | 100 | 99 |
|  | 2.2 | 100 | 100 | 100 | 100 | 100 | 99 |
| 16 | 1.1 | 98 | 95 | 98 | 100 | 100 | 100 |
|  | 2.2 | 100 | 100 | 100 | 100 | 100 | 100 |
| 17 | 1.1 | 100 | 98 | 100 | 98 | 99 | 100 |
|  | 2.2 | 100 | 100 | 100 | 100 | 100 | 100 |
| 18 | 0.56 | 100 | 99 | 98 | 99 | 99 | 100 |
|  | 1.1 | 100 | 100 | 100 | 100 | 100 | 100 |
| 19 | 0.56 | 99 | 98 | 100 | 98 | 90 | 90 |
|  | 1.0 | 100 | 99 | 100 | 100 | 100 | 99 |
| 20 | 0.56 | 100 | 98 | 100 | 100 | 100 | 100 |
|  | 1.1 | 100 | 100 | 100 | 100 | 100 | 100 |
| 21 | 1.1 | 100 | 98 | 95 | 100 | 100 | 100 |
|  | 2.2 | 100 | 99 | 100 | 100 | 98 | 100 |
| 22 | 1.1 | 100 | 98 | 100 | 98 | 85 | 100 |
|  | 2.2 | 100 | 100 | 100 | 100 | 100 | 100 |
| 23 | 1.1 | 100 | 99 | 100 | 98 | 99 | 95 |
|  | 2.2 | 99 | 98 | 100 | 100 | 100 | 99 |
| 24 | 1.1 | 100 | 100 | 100 | 100 | 100 | 100 |
|  | 2.2 | 100 | 100 | 100 | 100 | 100 | 100 |
| 25 | 1.1 | 100 | 98 | 100 | 100 | 100 | 100 |
|  | 2.2 | 100 | 100 | 100 | 100 | 100 | 100 |
| 26 | 1.1 | 100 | 100 | 100 | 99 | 100 | 100 |
|  | 2.2 | 100 | 99 | 100 | 100 | 100 | 100 |
| 27 | 2.2 | 100 | 98 | 98 | 98 | 99 | 100 |
|  | 4.5 | 100 | 100 | 100 | 100 | 100 | 100 |
| 28 | 1.1 | 100 | 98 | 99 | 99 | 99 | 100 |
|  | 2.2 | 100 | 99 | 100 | 100 | 100 | 100 |
| 29 | 1.1 | 99 | 90 | 100 | 100 | 100 | 100 |
|  | 2.2 | 99 | 98 | 100 | 100 | 100 | 100 |
| 30 | 1.1 | 99 | 80 | 100 | 100 | 100 | 100 |
|  | 2.2 | 99 | 100 | 100 | 100 | 99 |  |
| 31 | 1.1 | 99 | 99 | 100 | 98 | 98 | 100 |
|  | 2.2 | 100 | 100 | 100 | 100 | 100 | 100 |
| 32 | 1.1 | 99 | 100 | 100 | 100 | 100 | 100 |
|  | 2.2 | 100 | 100 | 100 | 100 | 100 | 100 |
| 33 | 1.1 | 99 | 80 | 90 | 99 | 100 | 100 |
|  | 2.2 | 100 | 100 | 100 | 100 | 100 | 100 |
| 34 | 1.1 | 100 | 98 | 100 | 98 | 100 | 100 |
|  | 2.2 | 100 | 100 | 100 | 100 | 100 | 100 |
| 35 | 1.1 | 100 | 80 | 100 | 100 | 100 | 100 |
|  | 2.2 | 100 | 98 | 100 | 100 | 100 | 100 |
| 36 | 1.1 | 100 | 75 | 100 | 100 | 100 | 100 |
|  | 2.2 | 100 | 100 | 100 | 100 | 100 | 100 |
| 37 | 1.1 | 99 | 98 | 98 | 100 | 100 | 100 |
|  | 2.2 | 100 | 100 | 100 | 100 | 100 | 100 |

EXPERIMENT 4

At the conclusion of the herbicidal study described in Experiment 3, the apparent X and 2X rates for each of the compounds were selected and a study to determine the rate of degradation and residual activity of the compounds by bioassaying the soil at 30, 98, 150, 176, 239 and 314 days after the initial treatment applied in Experiment 3, was conducted. The procedure was essentially the same as described in Experiment 2, above. The last two dioassays (at 239 and 314 days, respectively) were conducted using the same soil as was used for the third bioassay at 150 days and for the fourth bioassay at 176 days, respectively. The results are set forth in Chart 4, which follows.

Chart 4

Percent Control

| Cmp. | kg./ha. | Wheat 0 | Wheat 30 | Wheat 98 | Wheat 150 | Wheat 176 | Wheat 239 | Wheat 314 | Mustard 0 | Mustard 30 | Mustard 98 | Mustard 150 | Mustard 176 | Mustard 239 | Mustard 314 | Sorghum 0 | Sorghum 30 | Sorghum 98 | Sorghum 150 | Sorghum 176 | Sorghum 239 | Sorghum 314 |
|---|---|---|---|---|---|---|---|---|---|---|---|---|---|---|---|---|---|---|---|---|---|---|
| 1 | 1.1 | 100 | 98 | 98 | 98 | 100 | 30 | 40 | 98 | 95 | 100 | 100 | 100 | 60 | 45 | 90 | 70 | 40 | 40 | 50 | 10 | 0 |
|  | 2.2 | 99 | 100 | 98 | 100 | 100 | 90 | 90 | 100 | 98 | 100 | 100 | 100 | 99 | 98 | 80 | 70 | 70 | 70 | 98 | 10 | 40 |
| 5 | 0.56 | 99 | 99 | 100 | 99 | 100 | 40 | 55 | 100 | 100 | 100 | 100 | 100 | 100 | 99 | 80 | 80 | 70 | 75 | 50 | 20 | 50 |
|  | 1.1 | 100 | 95 | 100 | 100 | 99 | 100 | 100 | 100 | 95 | 100 | 100 | 100 | 100 | 100 | 80 | 100 | 60 | 90 | 70 | 70 | 80 |
| 7 | 0.56 | 99 | 99 | 98 | 100 | 100 | 50 | 85 | 100 | 100 | 100 | 100 | 100 | 99 | 100 | 99 | 85 | 60 | 80 | 70 | 30 | 60 |
|  | 1.1 | 100 | 99 | 99 | 100 | 100 | 95 | 100 | 100 | 100 | 100 | 100 | 100 | 100 | 100 | 100 | 98 | 100 | 98 | 100 | 60 | 50 |
|  | 2.2 | 100 | 99 | 100 | 100 | 100 | 100 | 100 | 100 | 100 | 100 | 100 | 100 | 100 | 100 | 100 | 100 | 80 | 100 | 100 | 40 | 98 |
| 12 | 0.56 | 100 | 99 | 99 | 100 | 100 | 50 | 60 | 100 | 70 | 100 | 100 | 100 | 99 | 100 | 95 | 65 | 50 | 50 | 85 | 50 | 30 |
|  | 1.1 | 100 | 99 | 99 | 100 | 100 | 99 | 99 | 100 | 98 | 100 | 100 | 100 | 99 | 100 | 100 | 85 | 90 | 70 | 80 | 80 | 40 |
|  | 2.2 | 100 | 98 | 70 | 100 | 97 | 30 | 35 | 100 | 98 | 100 | 100 | 100 | 99 | 100 | 95 | 100 | 70 | 100 | 100 | 40 | 80 |
| 13 | 0.56 | 100 | 80 | 99 | 100 | 100 | 85 | 85 | 100 | 99 | 100 | 100 | 100 | 99 | 100 | 100 | 80 | 95 | 60 | 65 | 40 | 20 |
|  | 1.1 | 100 | 95 | 99 | 100 | 100 | 98 | 90 | 100 | 100 | 100 | 100 | 100 | 100 | 100 | 99 | 100 | 70 | 100 | 100 | 80 | 75 |
|  | 2.2 | 100 | 100 | 99 | 100 | 100 | 30 | 5 | 100 | 100 | 100 | 100 | 100 | 20 | 0 | 80 | 70 | 95 | 100 | 0 | 0 | 100 |
| 14 | 1.1 | 100 | 90 | 75 | 95 | 85 | 40 | 20 | 80 | 90 | 0 | 30 | 0 | 10 | 100 | 100 | 100 | 100 | 30 | 0 | 20 | 5 |
|  | 2.2 | 100 | 98 | 99 | 98 | 95 | 30 | 50 | 100 | 98 | 95 | 40 | 70 | 99 | 100 | 100 | 70 | 80 | 50 | 75 | 0 | 10 |
| 15 | 1.1 | 98 | 90 | 90 | 100 | 100 | 50 | 40 | 100 | 98 | 100 | 100 | 100 | 99 | 100 | 100 | 90 | 80 | 80 | 95 | 60 | 0 |
|  | 2.2 | 100 | 98 | 99 | 95 | 99 | 60 | 60 | 100 | 98 | 100 | 100 | 100 | 99 | 99 | 80 | 95 | 80 | 80 | 75 | 10 | 50 |
| 16 | 1.1 | 100 | 90 | 70 | 100 | 80 | 20 | 35 | 100 | 100 | 100 | 100 | 100 | 100 | 100 | 100 | 75 | 50 | 60 | 100 | 30 | 70 |
|  | 2.2 | 98 | 95 | 70 | 100 | 100 | 50 | 90 | 98 | 100 | 100 | 100 | 100 | 100 | 100 | 100 | 100 | 30 | 85 | 98 | 50 | 70 |
| 17 | 1.1 | 100 | 90 | 99 | 100 | 100 | 60 | 45 | 100 | 90 | 100 | 100 | 100 | 100 | 99 | 98 | 100 | 50 | 100 | 100 | 90 | 30 |
|  | 2.2 | 100 | 98 | 98 | 50 | 40 | 90 | 99 | 100 | 100 | 100 | 100 | 20 | 10 | 0 | 100 | 20 | 30 | 30 | 10 | 0 | 70 |
| 18 | 0.56 | 99 | 90 | 60 | 40 | 75 | 30 | 5 | 99 | 50 | 0 | 5 | 0 | 0 | 100 | 99 | 70 | 0 | 30 | 30 | 0 | 0 |
|  | 1.1 | 100 | 80 | 70 | 95 | 30 | 20 | 10 | 100 | 20 | 50 | 5 | 20 | 0 | 0 | 98 | 80 | 40 | 20 | 40 | 20 | 5 |
| 19 | 0.56 | 99 | 98 | 20 | 90 | 98 | 40 | 5 | 90 | 50 | 0 | 100 | 10 | 20 | 10 | 98 | 98 | 60 | 60 | 85 | 80 | 0 |
|  | 1.1 | 100 | 85 | 95 | 40 | 100 | 50 | 10 | 100 | 20 | 50 | 100 | 30 | 100 | 100 | 99 | 95 | 90 | 100 | 98 | 30 | 50 |
| 20 | 0.56 | 99 | 98 | 90 | 98 | 100 | 80 | 60 | 100 | 50 | 100 | 100 | 100 | 100 | 100 | 100 | 100 | 60 | 100 | 95 | 85 | 90 |
|  | 1.1 | 100 | 100 | 99 | 98 | 100 | 60 | 75 | 99 | 100 | 100 | 100 | 100 | 100 | 100 | 98 | 70 | 80 | 100 | 100 | 30 | 90 |
| 21 | 1.1 | 100 | 98 | 80 | 100 | 100 | 95 | 50 | 90 | 98 | 100 | 100 | 100 | 100 | 10 | 98 | 85 | 70 | 85 | 50 | 20 | 60 |
| 22 | 2.2 | 100 | 60 | 95 | 40 | 40 | 30 | 75 | 100 | 20 | 10 | 20 | 30 | 10 | 10 | 98 | 40 | 40 | 30 | 0 | 20 | 45 |
| 23 | 2.2 | 100 | 98 | 20 | 98 | 100 | 30 | 10 | 100 | 50 | 99 | 98 | 100 | 20 | 0 | 99 | 98 | 0 | 70 | 50 | 20 | 0 |
|  | 1.1 | 99 | 60 | 70 | 5 | 20 | 30 | 45 | 99 | 100 | 0 | 0 | 0 | 75 | 5 | 98 | 100 | 50 | 30 | 0 | 0 | 0 |
| 24 | 2.2 | 100 | 98 | 0 | 90 | 50 | 10 | 10 | 100 | 20 | 65 | 85 | 30 | 60 | 10 | 100 | 40 | 20 | 10 | 50 | 20 | 5 |
| 25 | 1.1 | 100 | 10 | 75 | 5 | 30 | 0 | 5 | 100 | 50 | 99 | 98 | 98 | 90 | 95 | 98 | 85 | 30 | 20 | 0 | 10 | 5 |
| 26 | 2.2 | 100 | 80 | 40 | 90 | 95 | 20 | 80 | 98 | 20 | 10 | 5 | 30 | 100 | 100 | 99 | — | 30 | 40 | 30 | 20 | 25 |
| 27 | 1.1 | 100 | 98 | 99 | 100 | 99 | 30 | 20 | 100 | 65 | 100 | 100 | 100 | 10 | 0 | 100 | 80 | 50 | 60 | 75 | 40 | 45 |
|  | 2.2 | 100 | 100 | 0 | 75 | 100 | 70 | 30 | 99 | 98 | 0 | 60 | 30 | 30 | 80 | 98 | 100 | 20 | 100 | 100 | 0 | 5 |
|  | 4.5 | 100 | 95 | 40 | 98 | 40 | 50 | 65 | 100 | 20 | 90 | 5 | 10 | 0 | 10 | 98 | 75 | 50 | 20 | 20 | 20 | 5 |
| 28 | 1.1 | 100 | 80 | 99 | 60 | 20 | 30 | 98 | 98 | 80 | 0 | 60 | 30 | 20 | 0 | 100 | 95 | 99 | 10 | 95 | 0 | 25 |
| 29 | 2.2 | 100 | 85 | 60 | 98 | 90 | 30 | 25 | 100 | 98 | 90 | 5 | 20 | 10 | 40 | 98 | 70 | 20 | 90 | 20 | 0 | 65 |
| 39 | 1.1 | 99 | 80 | 95 | 30 | 20 | 30 | 50 | 80 | 60 | 20 | 100 | 20 | 20 | 0 | 80 | 90 | 75 | 10 | 70 | 0 | 5 |
|  | 2.2 | 99 | 98 | 10 | 50 | 40 | 30 | 70 | 100 | 60 | 0 | 60 | 20 | 0 | 5 | 90 | 0 | 20 | 60 | 0 | 0 | 60 |
| 31 | 1.1 | 99 | 85 | 30 | 50 | 10 | 30 | 20 | 98 | 30 | 0 | 0 | 10 | 20 | 0 | 99 | 80 | 30 | 0 | 10 | 20 | 0 |

-continued

Chart 4

| Cmp. | kg./ha. | Wheat | | | | | | | Percent Control Mustard | | | | | | | Sorghum | | | | | | |
|---|---|---|---|---|---|---|---|---|---|---|---|---|---|---|---|---|---|---|---|---|---|---|
| | | 0 | 30 | 98 | 150 | 176 | 239 | 314 | 0 | 30 | 98 | 150 | 176 | 239 | 314 | 0 | 30 | 98 | 150 | 176 | 239 | 314 |
| 32 | 2.2 | 100 | 98 | 90 | 98 | 70 | 30 | 30 | 100 | 80 | 99 | 10 | 40 | 10 | 0 | 100 | 98 | 70 | 60 | 70 | 20 | 10 |
| | 1.1 | 99 | 70 | 30 | 60 | 10 | 20 | 5 | 100 | 40 | 0 | 0 | 0 | 0 | 0 | 100 | 70 | 20 | 20 | 20 | 0 | 5 |
| 33 | 2.2 | 100 | 98 | 60 | 98 | 90 | 10 | 25 | 100 | 70 | 85 | 85 | 99 | 0 | 0 | 100 | 80 | 60 | 70 | 80 | 10 | 20 |
| | 1.1 | 99 | 80 | 10 | 70 | 30 | 5 | 20 | 100 | 65 | 0 | 20 | 30 | 5 | 0 | 80 | 65 | 30 | 10 | 20 | 0 | 0 |
| 34 | 2.2 | 100 | 90 | 99 | 98 | 80 | 30 | 40 | 100 | — | 100 | 100 | 100 | 20 | 0 | 100 | 100 | 60 | 70 | 50 | 20 | 40 |
| | 1.1 | 100 | 100 | 99 | 100 | 100 | 100 | 90 | 100 | 100 | 100 | 100 | 100 | 100 | 100 | 98 | 90 | 80 | 85 | 50 | 40 | 50 |
| 35 | 2.2 | 100 | 100 | 100 | 100 | 100 | 100 | 100 | 100 | 100 | 100 | 100 | 100 | 99 | 100 | 100 | 98 | 90 | 85 | 85 | 60 | 65 |
| | 1.1 | 100 | 100 | 100 | 98 | 100 | 75 | 75 | 100 | 80 | 100 | 100 | 100 | 100 | 100 | 80 | 80 | 50 | 70 | 10 | 20 | 40 |
| 36 | 2.2 | 100 | 100 | 99 | 100 | 100 | 100 | 98 | 100 | 98 | 100 | 100 | 100 | 99 | 100 | 100 | 60 | 70 | 90 | 90 | 40 | 60 |
| | 1.1 | 100 | 100 | 99 | 98 | 98 | 80 | 65 | 75 | 80 | 100 | 100 | 100 | 100 | 99 | 75 | 10 | 10 | 40 | 0 | 30 | 0 |
| 37 | 2.2 | 99 | 100 | 100 | 99 | 95 | 60 | 85 | 100 | 90 | 100 | 100 | 100 | 80 | 5 | 98 | 85 | 40 | 80 | 85 | 0 | 10 |
| | 1.1 | 100 | 100 | 100 | 100 | 99 | 100 | 45 | 100 | 100 | 100 | 100 | 100 | 100 | 90 | 100 | 100 | 70 | 85 | 60 | 30 | 30 |

Field trials of the efficacy of compounds coming within the scope of the generic formula (I), supra, in controlling the growth of undesirable vegetation in fallow wheatland were conducted and are illustrated by the procedures hereinafter set forth.

FIELD TRIAL 1

The following procedure was used to determine the herbicidal efficacy and crop tolerance of a number of thiadiazol-2-ylureas when surface applied to fallow wheatland that received a chisel operation soon after the harvesting of the wheat grown thereon.

The compounds tested were each formulated as a 50% wettable powder. Each compound was surface applied to a separate plot following the chiseling operation. This land was located in Colorado.

The experimental design was the complete randomized block. There were three replicates per treatment and each plot size was 3.65 by 9.14 meters. The previous crop grown on the sites was wheat. The herbicidal compositions were applied with a $CO_2$ sprayer mounted on a tractor.

Observations of the herbicidal effects of the test compounds began 29 days after treatment (DAT), and were repeated at intervals thereafter. The days of observation are indicated in the table.

The following is a list of all the plants observed in the field trials as carried out according to the procedure of this field trial, as well as the other field trials described hereinafter. The plants are identified by their common name and scientific name. Indicated abbreviations of the common names are used then to identify the plants in the tables which follow:

WHT Volunteer Wheat, *Triticum aestivum*
BAR Volunteer Barley, *Hordeum vulgare*
BYD Barnyardgrass, *Echinochloa crus-galli*
CHT Cheat, *Bromus secalinus*
CRB Crabgrass, *Digitaria sanguinalis*
DBR Downy Brome, *Bromus tectorum*
FOX Green Foxtail, *Setaria viridis*
STK Stinkgrass, *Eragrostis cilianensis*
WTG Witchgrass, *Panicum capillare*
BUF Buffalobur, *Solanum rostratum*
DAN Common Dandelion, *Taraxacum officinale*
PUR Common Purslane, *Portulaca oleracea*
TAR Fiddleneck Tarweed, *Amsinckia lycopsoides*
KOC Kochia, *Kochia scoparia*
PIG Redroot Pigweed, *Amaranthus retroflexus*
PSG Pitchers Sage, *Salvia azurea*
PRL Prickly Lettuce, *Lactuca serriola*
RAG Ragweed, *Ambrosia artemisiifolia*
RUS Russian Thistle, *Salsola kali*
TWH Tall Waterhemp, *Amaranthus tuberculatos*
VEM Venice Mallow, *Hibiscus trionum*
BUK Wild buckwheat, Polygonum convolvulus
MUS Wild Mustard, Brassica kaber
SUN Common Sunflower, *Helianthus annuus*
LAM Common lambsquarters, *Chenopodium album*
BWA Broad leaves, winter annual
PHE Pheasants eye, *Adonis annua*
WAP Waterpod, *Ellisia nyctelea*
AFL Annula Fleabane, *Erigeron annuus*
TMS Tumble mustard, *Sisymbrium altissimum*
HMS Hedge mustard, *Sisymbrium officinale*
BMC Blue mustard, *Chorispera tenella*
TAM Tansymustard, *Descurania pinnata*
QUA Quackgrass, *Agropyron repens*
FBW Field bindweed, *Convolvulus arvensis*
HWD Horseweed, *Conyza canadensis*
VPW Virginia pepperweed, *Lepidium virginicum*
PIP Prostrate pigweed, *Amaranthus blitoides*
NRJ Noethern rockjasmine, *Androsace septentrionalis*
FLX Flixweed, *Descurainia sophia*
FPC Field pennycress, *Thlaspi arvense*
WIO Wild Oat, *Avena fatua*
SPP Speedwell purslane, *Veronica peregrina*
FTB Foxtail barley, *Hordeum jubatum*

On day 286 after treatment, all treatments except Compounds 7 and 12 at 1.12, 1.68, and 2.24 kg./ha., were tilled with a tandem disc. In addition, all plots were tilled with a tandem disc to a depth of about 12.7 cm. at 8 km./hr. at 320 days after treatment.

The results of this field trial are set forth in Table 1, which follows. In the table, column 1 identifies the compound by number; column 2 the application rate of each herbicide in kilograms per hectare; and the remaining columns list the percent control of volunteer wheat and the numerous weed species at the indicated days after treatment.

Table 1

Percent Control of Volunteer Wheat and Weeds at Indicated Days After Treatment

| Cmp. | kg./ha. | 29 WHT | STK | PIG | RUS | PUR | 82 WHT | 104 WHT | 209 WHT | 260 WHT | CHT | MUS | 278 WHT | CHT | TUS | MUS | KOC | 320 PIG | RUS | KOC |
|---|---|---|---|---|---|---|---|---|---|---|---|---|---|---|---|---|---|---|---|---|
| 2 | 0.56 | 20 | 10 | 13 | 3 | 3 | 17 | 78 | 53 | 0 | 0 | 0 | 10 | 17 | 0 | 30 | 30 | 0 | 0 | 33 |
|   | 1.12 | 20 | 10 | 10 | 3 | 10 | 33 | 82 | 57 | 0 | 0 | 0 | 17 | 20 | 0 | 33 | 0 | 67 | 27 | 67 |
|   | 1.68 | 33 | 17 | 17 | 3 | 23 | 40 | 78 | 52 | 0 | 0 | 0 | 10 | 10 | 20 | 33 | 33 | 100 | 67 | 100 |
|   | 2.24 | 72 | 53 | 63 | 17 | 43 | 43 | 87 | 85 | 73 | 83 | 97 | 30 | 37 | 0 | 67 | 43 | 100 | 55 | 67 |
| 3 | 0.56 | 53 | 20 | 33 | 0 | 30 | 17 | 80 | 68 | 23 | 10 | 30 | 0 | 0 | 20 | 0 | 0 | 67 | 30 | 67 |
|   | 1.12 | 57 | 27 | 60 | 13 | 33 | 40 | 86 | 37 | 0 | 0 | 0 | 27 | 37 | 37 | 67 | 60 | 100 | 92 | 100 |
|   | 1.68 | 60 | 17 | 47 | 10 | 33 | 47 | 80 | 47 | 23 | 33 | 33 | 30 | 30 | 20 | 67 | 33 | 67 | 65 | 67 |
|   | 2.24 | 67 | 20 | 33 | 7 | 27 | 50 | 83 | 77 | 23 | 33 | 33 | 38 | 50 | 23 | 67 | 67 | 99 | 93 | 100 |
| 7 | 0.56 | 37 | 17 | 30 | 0 | 23 | 3 | 60 | 67 | 38 | 60 | 67 | 50 | 68 | 50 | 100 | 67 | 100 | 98 | 100 |
|   | 1.12 | 40 | 23 | 35 | 7 | 27 | 27 | 77 | 80 | 67 | 80 | 97 | 72 | 82 | 69 | 100 | 100 | 100 | 99 | 100 |
|   | 1.68 | 40 | 0 | 3 | 0 | 0 | 50 | 82 | 87 | 94 | 100 | 100 | 96 | 100 | 98 | 100 | 100 | 100 | 97 | 100 |
|   | 2.24 | 77 | 37 | 70 | 13 | 57 | 68 | 92 | 97 | 99 | 100 | 100 | 98 | 100 | 96 | 100 | 100 | 100 | 93 | 100 |
| 12 | 0.56 | 13 | 3 | 7 | 0 | 10 | 10 | 78 | 77 | 40 | 90 | 100 | 40 | 47 | 23 | 93 | 90 | 100 | 95 | 100 |
|   | 1.12 | 43 | 20 | 30 | 0 | 27 | 50 | 85 | 83 | 93 | 100 | 100 | 96 | 99 | 94 | 100 | 100 | 100 | 27 | 100 |
|   | 1.68 | 43 | 17 | 17 | 0 | 10 | 47 | 91 | 99 | 98 | 100 | 100 | 98 | 100 | 82 | 100 | 100 | 100 | 52 | 100 |
|   | 2.24 | 88 | 70 | 85 | 33 | 67 | 82 | 96 | 97 | 99 | 100 | 100 | 99 | 100 | 95 | 100 | 100 | 100 | 33 | 100 |
| 13 | 0.56 | 27 | 7 | 10 | 0 | 13 | 7 | 82 | 73 | 23 | 30 | 33 | 17 | 23 | 0 | 67 | 67 | 66 | 63 | 67 |
|   | 1.12 | 30 | 7 | 7 | 0 | 7 | 20 | 78 | 83 | 72 | 73 | 77 | 70 | 83 | 63 | 100 | 77 | 100 | 93 | 100 |
|   | 1.68 | 23 | 7 | 17 | 0 | 17 | 40 | 85 | 78 | 90 | 100 | 97 | 82 | 93 | 89 | 99 | 100 | 100 | 100 | 100 |
|   | 2.24 | 33 | 0 | 0 | 0 | 0 | 40 | 72 | 85 | 97 | 100 | 100 | 98 | 100 | 99 | 100 | 100 | 100 | 100 | 100 |
| Control | 0 | 0 | 0 | 0 | 0 | 0 | 0 | 0 | 0 | 0 | 0 | 0 | 0 | 0 | 0 | 0 | 0 | 0 | 0 | 0 |

On the 395th day after treatment, wheat, variety Centurk, was planted to a depth of 10 cm. at a rate of 26.4 kg./ha., with a 19.5 m. hoe drill. The total amount of rainfall between time of treating until time of seeding wheat, a period of 13 months, was 26.4 cm.

Observations were then made of the early wheat 32 days after seeding (427 days after treatment) and 53 days after seeding (448 days after treatment) to determine the percent injury of the wheat. Also included in Table 2 is the yield of wheat, which yield is recorded as percent of Control, at 706 DAT, where control=100%. All this information is recorded in Table 2, which follows. The test compounds are identified in the same manner as described supra. In the table, column 1 identifies the test compound; column 2 records the original application rate of the herbicides in kilograms per hectare; columns 3 and 4 list the percent injury at the indicated days after treatment (DAT); and column 5 lists the yield of wheat as Percent of Control at 706 DAT.

Table 2

| Compound | Rate kg./ha. | Percent Crop Injury 427 DAT | 448 DAT | Crop Yield % of Control 706 DAT |
|---|---|---|---|---|
| 2 | 0.56 | 0 | 0 | 101 |
|   | 1.12 | 0 | 0 | 93 |
|   | 1.68 | 7 | 10 | 99 |
|   | 2.24 | 10 | 10 | 93 |
| 3 | 0.56 | 0 | 0 | 99 |
|   | 1.12 | 0 | 10 | 100 |
|   | 1.68 | 0 | 10 | 95 |
|   | 2.24 | 20 | 40 | 93 |
| 7 | 0.56 | 3 | 0 | 96 |
|   | 1.12 | 3 | 20 | 87 |
|   | 1.68 | 23 | 23 | 59 |
|   | 2.24 | 30 | 17 | 55 |
| 12 | 0.56 | 0 | 7 | 96 |
|   | 1.12 | 0 | 17 | 94 |
|   | 1.68 | 13 | 10 | 100 |
|   | 2.24 | 3 | 10 | 83 |
| 13 | 0.56 | 10 | 10 | 101 |

Table 2-continued

| Compound | Rate kg./ha. | Percent Crop Injury 427 DAT | 448 DAT | Crop Yield % of Control 706 DAT |
|---|---|---|---|---|
|   | 1.12 | 3 | 20 | 88 |
|   | 1.68 | 0 | 0 | 100 |
|   | 2.24 | 17 | 10 | 74 |

FIELD TRIAL 2

The following procedure was used to determine the herbicidal efficacy of the same compounds tested in Field Trial 1, and to determine the crop tolerance of winter wheat after fallow when these compounds were surface applied to fallow land following the wheat harvest. This trial was run in Kansas.

The test compounds and the comparison compound were formulated in the same manner as described in Field Trial 1. The compounds were surface applied to land from which the wheat had just been harvested. Wheat stubble remained standing in the field.

The compounds were applied in the same manner as in the previous experiment. There was no soil incorporation of the compounds. The experimental design was the complete randomized block, and there were three replicates per treatment. Each plot measured 3.65 by 9.14 meters. The plots received 3.8 cm. of rainfall 2 days after application.

On the 285th day after treatment, all the treatments, except Compound 7 and Compound 12 at application rates of 1.12, 1.68, and 2.24 kg./ha., were tilled with a tandem disc.

Following the date of application of the test compounds, observations of the control of unwanted vegetation on the land by the test compounds were made at intervals. The control was rated on a scale of 0 to 100, the 0 meaning no control, and 100 meaning 100% control. The results are shown in Table 3, which follows.

Table 3

| | | Percent Control of Volunteer Wheat and Weeds at Indicated Days After Treatment | | | | | | | | | | | | | |
|---|---|---|---|---|---|---|---|---|---|---|---|---|---|---|---|
| | | 33 | | | | | | 102 | | | | | 278 | | |
| Cmp. | kg./ha. | WHT | STK | WTG | RUS | TWH | BUF | WHT | WHT | CHT | MUS | PRL | WHT | DBR | RUS |
| 2 | 0.56 | 0 | 0 | 0 | 0 | 0 | 0 | 60 | 0 | 0 | 0 | 0 | 0 | 0 | 0 |
|   | 1.12 | 72 | 57 | 67 | 0 | 10 | 10 | 68 | 43 | 37 | 57 | 30 | 83 | 50 | 17 |
|   | 1.68 | 95 | 90 | 92 | 0 | 23 | 0 | 82 | 83 | 83 | 98 | 63 | 73 | 42 | 23 |
|   | 2.24 | 92 | 78 | 78 | 0 | 37 | 40 | 75 | 95 | 100 | 100 | 98 | 97 | 97 | 77 |
| 3 | 0.56 | 53 | 30 | 23 | 10 | 0 | 0 | 58 | 0 | 0 | 0 | 0 | 0 | 0 | 0 |
|   | 1.12 | 78 | 63 | 67 | 0 | 33 | 0 | 76 | 47 | 43 | 67 | 63 | 40 | 37 | 13 |
|   | 1.68 | 75 | 72 | 72 | 10 | 33 | 0 | 72 | 33 | 40 | 60 | 23 | 0 | 0 | 0 |
|   | 2.24 | 83 | 72 | 77 | 0 | 0 | 0 | 73 | 80 | 75 | 100 | 97 | 84 | 83 | 40 |
| 7 | 0.56 | 93 | 75 | 82 | 20 | 57 | 0 | 95 | 93 | 99 | 100 | 60 | 99 | 99 | 80 |
|   | 1.12 | 97 | 97 | 93 | 0 | 20 | 30 | 93 | 95 | 98 | 100 | 97 | 97 | 100 | 90 |
|   | 1.68 | 99 | 95 | 95 | 68 | 85 | 96 | 93 | 100 | 100 | 100 | 100 | 100 | 100 | 99 |
|   | 2.24 | 100 | 100 | 98 | 53 | 92 | 98 | 93 | 100 | 100 | 100 | 100 | 100 | 100 | 97 |
| 12 | 0.56 | 87 | 63 | 63 | 20 | 37 | 0 | 93 | 87 | 83 | 90 | 67 | 77 | 46 | 43 |
|   | 1.12 | 97 | 92 | 92 | 27 | 30 | 57 | 96 | 99 | 100 | 100 | 99 | 100 | 100 | 78 |
|   | 1.68 | 98 | 93 | 95 | 20 | 67 | 85 | 97 | 100 | 100 | 100 | 100 | 100 | 100 | 98 |
|   | 2.24 | 98 | 98 | 98 | 57 | 95 | 100 | 96 | 100 | 100 | 100 | 100 | 100 | 100 | 100 |
| 13 | 0.56 | 93 | 80 | 80 | 0 | 53 | 0 | 76 | 68 | 59 | 63 | 57 | 52 | 33 | 28 |
|   | 1.12 | 95 | 92 | 90 | 10 | 27 | 13 | 80 | 89 | 87 | 100 | 90 | 91 | 94 | 88 |
|   | 1.68 | 97 | 93 | 93 | 27 | 70 | 92 | 90 | 89 | 93 | 100 | 100 | 99 | 100 | 92 |
|   | 2.24 | 100 | 97 | 100 | 67 | 90 | 100 | 53 | 99 | 100 | 100 | 100 | 100 | 100 | 100 |
| Control | 0 | 0 | 0 | 0 | 0 | 0 | 0 | 0 | 0 | 0 | 0 | 0 | 0 | 0 | 0 |

| | | Percent Control of Volunteer Wheat and Weeds at Indicated Days After Treatment | | | | | | | | | | | | |
|---|---|---|---|---|---|---|---|---|---|---|---|---|---|---|
| | | 278 | | | 306 | | | | | | | 341 | | | |
| Cmp. | kg./ha. | MUS | PRL | BUF | WHT | DBR | CRB | RUS | PRL | MUS | BUF | CRB | FOX | BUF | STK | PIG | RUS |
| 2 | 0.56 | 0 | 0 | 0 | —* | — | — | — | — | — | — | 0 | 0 | 0 | 0 | 0 | 0 |
|   | 1.12 | 67 | 37 | 20 | — | — | — | — | — | — | — | 0 | 0 | 0 | 0 | 0 | 0 |

Table 3-continued

| | | | | | | | | | | | | | | | | | | | |
|---|---|---|---|---|---|---|---|---|---|---|---|---|---|---|---|---|---|---|---|
| | 1.68 | 93 | 47 | 17 | — | — | — | — | — | — | — | 0 | 0 | 33 | 0 | 27 | 33 |
| | 2.24 | 100 | 100 | 87 | — | — | — | — | — | — | — | 73 | 80 | 100 | 83 | 91 | 99 |
| 3 | 0.56 | 0 | 0 | 0 | — | — | — | — | — | — | — | 0 | 0 | 0 | 0 | 0 | 0 |
| | 1.12 | 67 | 67 | 47 | — | — | — | — | — | — | — | 73 | 83 | 100 | 87 | 88 | 98 |
| | 1.68 | 0 | 0 | 0 | — | — | — | — | — | — | — | 91 | 97 | 100 | 93 | 97 | 98 |
| | 2.24 | 100 | 83 | 27 | — | — | — | — | — | — | — | 95 | 100 | 100 | 100 | 96 | 100 |
| 7 | 0.56 | 100 | 79 | 63 | — | — | — | — | — | — | — | 89 | 96 | 100 | 100 | 89 | 98 |
| | 1.12 | 99 | 98 | 63 | 96 | 98 | 82 | 63 | 92 | 100 | 97 | 98 | 100 | 100 | 100 | 99 | 32 |
| | 1.68 | 100 | 100 | 100 | 100 | 100 | 99 | 95 | 100 | 100 | 100 | 95 | 100 | 100 | 100 | 99 | 100 |
| | 2.24 | 100 | 100 | 93 | 100 | 100 | 97 | 98 | 100 | 100 | 100 | 100 | 100 | 100 | 100 | 100 | 100 |
| 12 | 0.56 | 67 | 63 | 60 | —* | — | — | — | — | — | — | 10 | 30 | 33 | 30 | 30 | 30 |
| | 1.12 | 100 | 100 | 75 | 99 | 100 | 80 | 60 | 100 | 100 | 100 | 58 | 70 | 100 | 77 | 97 | 0 |
| | 1.68 | 100 | 100 | 98 | 100 | 100 | 98 | 92 | 100 | 100 | 100 | 76 | 90 | 100 | 97 | 99 | 94 |
| | 2.24 | 100 | 100 | 99 | 100 | 100 | 98 | 91 | 100 | 100 | 100 | 99 | 100 | 100 | 100 | 100 | 97 |
| 13 | 0.56 | 33 | 33 | 30 | —* | — | — | — | — | — | — | 53 | 60 | 96 | 63 | 73 | 96 |
| | 1.12 | 100 | 97 | 85 | — | — | — | — | — | — | — | 97 | 97 | 100 | 100 | 97 | 99 |
| | 1.68 | 100 | 100 | 93 | — | — | — | — | — | — | — | 100 | 100 | 100 | 100 | 100 | 100 |
| | 2.24 | 100 | 100 | 97 | — | — | — | — | — | — | — | 99 | 100 | 100 | 100 | 99 | 100 |
| Control | 0 | 0 | 0 | 0 | 0 | 0 | 0 | 0 | 0 | 0 | 0 | 0 | 0 | 0 | 0 | 0 | 0 |

*No reading made.

On day 319 and day 342 after treatment, all plots were undercut with a Noble blade, and then all plots were rodweeded on the 390th day after treatment. On the 394th day after treatment, wheat, variety Scout, was planted to a depth of 5.1 cm. at a rate of 32.48 kg./ha. with a 14.6 meter press drill. The total rainfall from time of treatment until seeding the wheat, a period of 13 months, was 37.37 cm.

When the wheat was about 7.6 cm. tall, a height which the wheat reached 33 days after planting (427 DAT), an observation to determine the percent injury was made. This observation was repeated at the time when the wheat was about 15.34 cm. tall, which occurred 53 days after planting (447 DAT). The results of these observations of percent injury are recorded in Table 4, which follows. The test compounds are identified in the same manner as described supra.

Table 4

| Compound | Rate kg./ha. | Percent 427 DAT | Injury 447 DAT |
|---|---|---|---|
| 2 | 0.56 | 0 | 0 |
| | 1.12 | 0 | 0 |
| | 1.68 | 0 | 0 |
| | 2.24 | 0 | 0 |
| 3 | 0.56 | 0 | 0 |
| | 1.12 | 0 | 0 |
| | 1.68 | 0 | 0 |
| | 2.24 | 0 | 7 |
| 7 | 0.56 | 0 | 0 |
| | 1.12 | 0 | 0 |
| | 1.68 | 17 | 0 |
| | 2.24 | 17 | 7 |
| 12 | 0.56 | 0 | 0 |
| | 1.12 | 3 | 0 |
| | 1.68 | 13 | 0 |
| | 2.24 | 33 | 17 |
| 13 | 0.56 | 0 | 0 |
| | 1.12 | 0 | 0 |
| | 1.68 | 0 | 0 |
| | 2.24 | 0 | 0 |

FIELD TRIAL 3

This field trial, like Field Trial 1, was conducted in Colorado.

The same test compounds formulated in the same manner, but with the addition of ½% surfactant as tank mix, were applied in the same manner as in the previous field trials. The plots received a total of 27.9 cm. of rainfall after application of the herbicides until seeding in the following year. In addition, the plots were flood irrigated 37 days after treatment and 69 days after treatment, with approximately 5.08 cm. of water each date.

The percent control of volunteer barley and other weeds at the indicated days after treatment is recorded in Table 5, which follows.

Table 5

Percent Control of Volunteer Barley and Weeds at Indicated Days After Treatment

| Cmp. | kg./ha. | 32 | | | | | | 57 | 89 | 264 | | | BAR | FOX | 291 | | | BAR | 308 | | BAR | FOX | 321 | PIG |
|---|---|---|---|---|---|---|---|---|---|---|---|---|---|---|---|---|---|---|---|---|---|---|---|---|
| | | BAR | FOX | BYD | KOC | VEM | PSG | BAR | BAR | BAR | KOC | BUK | | | KOC | BUK | SUN | | FOX | KOC | | | KOC | |
| 2 | 1.12 | 50 | 78 | 65 | 70 | 55 | 55 | 70 | 0 | 30 | 0 | 50 | 0 | 0 | 0 | 0 | 0 | 0 | 78 | 40 | 0 | 0 | 0 | 0 |
| | 2.24 | 55 | 60 | 70 | 70 | 50 | 55 | 88 | 93 | 50 | 50 | 50 | 0 | 0 | 0 | 0 | 0 | 20 | 0 | 70 | 25 | 25 | 40 | 30 |
| 3 | 1.12 | 55 | 50 | 60 | 75 | 65 | 65 | 70 | 25 | 0 | 0 | 0 | 0 | 0 | 0 | 0 | 0 | 0 | 45 | 35 | 25 | 25 | 40 | 40 |
| | 2.24 | 15 | 50 | 45 | 45 | 45 | 45 | 48 | 0 | 40 | 30 | 40 | 50 | 0 | 90 | 0 | 0 | 0 | 55 | 55 | 25 | 25 | 40 | 40 |
| 7 | 1.12 | 90 | 100 | 100 | 98 | 90 | 95 | 94 | 85 | 100 | 100 | 100 | 0 | 50 | 100 | 100 | 100 | 0 | 65 | 55 | 50 | 50 | 100 | 100 |
| | 2.24 | 94 | 100 | 100 | 100 | 100 | 100 | 98 | 100 | 100 | 74 | 100 | 100 | 100 | 100 | 100 | 100 | 100 | 100 | 100 | 100 | 100 | 100 | 100 |
| 12 | 1.12 | 35 | 50 | 45 | 50 | 45 | 55 | 60 | 95 | 100 | 99 | 90 | 100 | 0 | 100 | 100 | 100 | 95 | 70 | 73 | 25 | 25 | 50 | 65 |
| | 2.24 | 95 | 95 | 100 | 100 | 98 | 95 | 94 | 100 | 100 | 50 | 50 | 80 | 50 | 95 | 100 | 100 | 50 | 90 | 100 | 90 | 90 | 100 | 100 |
| 13 | 1.12 | 64 | 93 | 85 | 80 | 80 | 80 | 80 | 48 | 50 | 99 | 100 | 100 | 48 | 100 | 100 | 100 | 100 | 70 | 65 | 40 | 40 | 45 | 50 |
| | 2.24 | 55 | 70 | 70 | 73 | 63 | 60 | 70 | 83 | 100 | 100 | 100 | 100 | 50 | 100 | 100 | 100 | 100 | 100 | 98 | 45 | 45 | 50 | 45 |
| Control | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

All the plots were tilled 308 days after treatment and again 334 days after treatment. Wheat, variety Colano, was planted 379 days after treatment, at a depth of 5.08 cm. at a rate of 67.2 kg./ha. with a 2.4 m. press drill.

The percent injury is recorded in Table 6, which follows.

volunteer rye. The test results are recorded in Table 7.

Table 7

| Cmp. | kg./ha. | Percent Control of Volunteer Wheat and Weeds at Indicated Days After Treatment | | | | | | | | | |
|---|---|---|---|---|---|---|---|---|---|---|---|
| | | 108 | | 140 | | 203 | | 218 | | 295 | | |
| | | WHT | DBR | WHT | DBR | WHT | DBR | WHT | DBR | WHT | DBR | TAR |
| 2 | 0.56 | 0 | 3 | 0 | 0 | 0 | 0 | 0 | 0 | 68 | 77 | 75 |
| | 1.12 | 0 | 7 | 0 | 3 | 2 | 2 | 0 | 0 | 77 | 77 | 100 |
| | 1.68 | 27 | 48 | 0 | 0 | 2 | 2 | 0 | 0 | 89 | 93 | 100 |
| | 2.24 | 33 | 57 | 0 | 5 | 3 | 3 | 0 | 0 | 96 | 99 | 100 |
| 3 | 0.56 | 0 | 12 | 0 | 0 | 0 | 0 | 0 | 0 | 48 | 48 | 100 |
| | 1.12 | 0 | 12 | 0 | 3 | 0 | 0 | 5 | 3 | 57 | 57 | 100 |
| | 1.68 | 0 | 15 | 0 | 2 | 0 | 0 | 5 | 8 | 55 | 58 | 97 |
| | 2.24 | 0 | 0 | 0 | 5 | 0 | 0 | 3 | 3 | 64 | 67 | 100 |
| 7 | 0.56 | 7 | 7 | 0 | 0 | 0 | 0 | 3 | 5 | 48 | 57 | 100 |
| | 1.12 | 7 | 7 | 0 | 5 | 3 | 3 | 32 | 32 | 90 | 95 | 100 |
| | 1.68 | 7 | 7 | 0 | 8 | 3 | 8 | 57 | 57 | 94 | 98 | 97 |
| | 2.24 | 7 | 7 | 0 | 28 | 20 | 20 | 82 | 83 | 98 | 99 | 100 |
| 12 | 0.56 | 0 | 0 | 0 | 5 | 0 | 0 | 10 | 10 | 68 | 47 | 100 |
| | 1.12 | 5 | 3 | 0 | 10 | 0 | 0 | 32 | 33 | 98 | 100 | 100 |
| | 1.68 | 3 | 15 | 0 | 13 | 0 | 0 | 60 | 57 | 99 | 100 | 100 |
| | 2.24 | 0 | 10 | 0 | 15 | 5 | 5 | 80 | 83 | 100 | 100 | 100 |
| 13 | 0.56 | 7 | 0 | 0 | 3 | 0 | 0 | 0 | 0 | 88 | 87 | 100 |
| | 1.12 | 7 | 5 | 0 | 7 | 0 | 0 | 8 | 7 | 95 | 100 | 100 |
| | 1.68 | 13 | 15 | 0 | 8 | 0 | 0 | 30 | 32 | 99 | 100 | 100 |
| | 2.24 | 7 | 18 | 0 | 8 | 0 | 0 | 45 | 45 | 100 | 100 | 100 |
| Control | 0 | 0 | 0 | 0 | 0 | 0 | 0 | 0 | 0 | 0 | 0 | 0 |

Table 6

| Cmp. | kg./ha. | Percent Injury 433 Early Wheat 5.08 cm. tall |
|---|---|---|
| 2 | 1.12 | 0 |
| | 2.24 | 0 |
| 3 | 1.12 | 0 |
| | 2.24 | 0 |
| 7 | 1.12 | 0 |
| | 2.24 | 0 |
| 12 | 1.12 | 0 |
| | 2.24 | 0 |
| 13 | 1.12 | 0 |
| | 2.24 | 0 |
| Control | 0 | 0 |

FIELD TRAIL 4

This field trial was conducted to study the herbicidal efficacy of the same test compounds as were used in the previous field trials, with this field trial being carried out in the state of Washington. In this field trial, the wheat stubble was disced once after the harvest of the wheat and then the test compounds were surface applied. Each test compound was formulated as a 50% wettable powder.

The first significant rainfall occurred about 3 months after treatment was applied and amounted to 0.6 cm. As of 203 days after treatment, the total rainfall totaled 10.5 cm.

Two hundred twenty-one days after treatment, the plots to which compounds 2, 3 and 13 had been applied were oversprayed with 1,1'-dimethyl-4,4'-bipyridinium dichloride at the rate of 2365 cc. of the herbicide dissolved in 283.7 l. of water, with 284 g. of a surfactant per hectare. In these plots, the volunteer wheat population was actually a mixture of volunteer wheat and volunteer rye. The test results are recorded in Table 7.

Four hundred and one days after treatment, the plot area was disced 10.16 to 15.24 cm. deep and rodweeded just prior to planting winter wheat, variety Wanser. The seeding rate was 44 kg./ha., planted 5.08 to 7.62 cm. deep by drill. By the time the first observation was made, the total rainfall on the plot was 18.44 cm. The experimental design was the randomized block with three replicates per treatment. The plots treated were 4.05 m. by 9.1 m. The percent injury is recorded in Table 8. Also included in the Table which follows is the yield of wheat recorded as Percent of Control, at 717 DAT, where Control=100%.

Table 8

| Cmp. | kg./ha. | Percent Injury at Indicated DAT | | Yield % of Control |
|---|---|---|---|---|
| | | 430 | 470 | 717 DAT |
| 2 | 0.56 | — | 7 | —* |
| | 1.12 | — | 8 | — |
| | 1.68 | — | 10 | — |
| | 2.24 | — | 10 | — |
| 3 | 0.56 | — | 0 | — |
| | 1.12 | — | 0 | — |
| | 1.68 | — | 3 | — |
| | 2.24 | — | 3 | — |
| 7 | 0.56 | 7 | 3 | 153 |
| | 1.12 | 18 | 8 | 157 |
| | 1.68 | 32 | 32 | 123 |
| | 2.24 | 35 | 37 | 66 |
| 12 | 0.56 | 15 | 8 | 102 |
| | 1.12 | 35 | 27 | 179 |
| | 1.68 | 55 | 45 | 281 |
| | 2.24 | 63 | 58 | 415 |
| 13 | 0.56 | — | 0 | 162 |
| | 1.12 | — | 7 | 64 |
| | 1.68 | — | 18 | 23 |
| | 2.24 | — | 25 | 0 |
| Control | 0 | 0 | 0 | |

*Plot not harvested.

FIELD TRIAL 5

This field trial was conducted in Indiana to determine the herbicidal efficacy of the same compounds used in the above field trials during a 12 to 13 month fallow period after the harvest of winter wheat. The compounds were applied to wheat stubble right after the winter wheat harvest. The experimental design was the randomized block with three replicates per rate of application. The plot size treated was 12.19 by 3.04 m.

The test compounds were applied over the surface to existing weeds, which were predominantly ragweed with some Venice mallow, large crabgrass and green foxtail, as well as the stubble left from the wheat harvest. The test compounds were each formulated as a 50 percent wettable powder. A surfactant, 0.1% of the total volume of each application treatment, was added to each treatment.

The test results are set forth in Table 9, in which are recorded the percent control of weeds at the indicated day after treatment; as well as the yield of wheat expressed as Percent of Control, wherein control=100%.

fallow land following the wheat harvest. This trial was run in Kansas.

The compounds tested were each formulated as an 80% wettable powder. Each compound was surface applied to a separate plot of land from which the wheat had just been harvested. Wheat stubble and weeds were standing in the field.

The compounds were applied in the same manner as in the previous field trials. There was no soil incorporation of the compounds. The experimental design was a complete randomized block, and there were 3 replicates per treatment. Each plot measured 3.66×21.3 meters, and the soil was loam of 2.9% organic content, as shown by testing.

On the 249th day after treatment, all of the treatments were sprayed with a mixture of 2-chloro-N-isopropylacetanilide and isooctyl ester of 2,4-dichlorophenoxyacetic acid, to destroy vegetation.

Following the date of application of the test com-

Table 9

| | | Percent Control of Weeds at Indicated Days After Treatment | | | | | | | | | | | | 706 |
|---|---|---|---|---|---|---|---|---|---|---|---|---|---|---|
| | | 41 | | | 104 | 270 | | 336 | | | | 365 | | Yield % |
| Cmp. | kg./ha. | FOX | RAG | AG* | WHT | WHT | DAN | AG* | DAN | VEM | RAG | AG* | DAN | RAG | of Control |
| 2 | 0.56 | 0 | 0 | 0 | 22 | 20 | 13 | 17 | 7 | 0 | 0 | 0 | 0 | 0 | 98 |
| | 1.12 | 7 | 10 | 0 | 17 | 23 | 17 | 10 | 0 | 0 | 0 | 20 | 0 | 42 | 94 |
| | 1.68 | 23 | 7 | 0 | 15 | 27 | 27 | 17 | 0 | 0 | 10 | 17 | 17 | 13 | 95 |
| | 2.24 | 47 | 60 | 13 | 13 | 13 | 0 | 0 | 7 | 7 | 20 | 7 | 0 | 32 | 102 |
| 3 | 0.56 | 7 | 57 | 17 | 10 | 35 | 18 | 0 | 20 | 10 | 20 | 0 | 25 | 28 | 116 |
| | 1.12 | 33 | 80 | 47 | 28 | 47 | 37 | 33 | 40 | 52 | 55 | 10 | 55 | 73 | 96 |
| | 1.68 | 47 | 82 | 33 | 32 | 37 | 30 | 52 | 63 | 83 | 92 | 7 | 28 | 86 | 90 |
| | 2.24 | 70 | 88 | 58 | 52 | 82 | 85 | 73 | 73 | 88 | 92 | 25 | 65 | 73 | 90 |
| 7 | 0.56 | 45 | 60 | 23 | 25 | 52 | 47 | 30 | 27 | 33 | 17 | 23 | 43 | 67 | 90 |
| | 1.12 | 50 | 88 | 50 | 37 | 68 | 77 | 60 | 45 | 77 | 82 | 25 | 47 | 65 | 90 |
| | 1.68 | 85 | 91 | 75 | 62 | 72 | 74 | 80 | 87 | 96 | 97 | 47 | 77 | 92 | 121 |
| | 2.24 | 95 | 98 | 88 | 83 | 92 | 94 | 81 | 93 | 97 | 97 | 67 | 90 | 95 | 115 |
| 12 | 0.56 | 23 | 10 | 0 | 23 | 17 | 17 | 13 | 37 | 13 | 13 | 7 | 30 | 40 | 100 |
| | 1.12 | 50 | 80 | 33 | 48 | 55 | 40 | 0 | 20 | 43 | 13 | 0 | 10 | 35 | 104 |
| | 1.68 | 70 | 80 | 50 | 58 | 87 | 77 | 47 | 33 | 70 | 77 | 17 | 47 | 77 | 110 |
| | 2.24 | 86 | 93 | 75 | 78 | 88 | 93 | 37 | 88 | 92 | 94 | 17 | 96 | 86 | 121 |
| 13 | 0.56 | 25 | 13 | 0 | 0 | 0 | 3 | 7 | 0 | 0 | 0 | 0 | 0 | 35 | 105 |
| | 1.12 | 47 | 53 | 20 | 20 | 13 | 17 | 0 | 23 | 20 | 30 | 0 | 30 | 40 | 84 |
| | 1.68 | 77 | 89 | 65 | 25 | 27 | 27 | 62 | 52 | 60 | 87 | 32 | 40 | 93 | 95 |
| | 2.24 | 94 | 93 | 63 | 37 | 63 | 75 | 63 | 67 | 88 | 93 | 13 | 37 | 92 | 93 |
| Control | 0 | 0 | 0 | 0 | 0 | 0 | 0 | 0 | 0 | 0 | 0 | 0 | 0 | 0 | 100 |

*Annual Grasses

FIELD TRIAL 6

The following procedure was used to determine the herbicidal efficacy of two of the same compounds previously tested in the above-described field trials and to determine the crop tolerance of winter wheat after fallow when these compounds were surface applied to pounds, observations of the control of unwanted vegetation on the land by the test compounds were made at intervals. Subsequently, on the 401st day after treatment with the test compounds, the plots were planted to winter wheat, variety Eagle and Scout, the seeding being carried out at a rate of 33.6 kg./ha. at a spacing of 0.3048 m. to a depth of 5 cm. The results of the application of the test compounds were observed and recorded and these results appear in Table 10 which follows.

Table 10

| | | Percent Control of Volunteer Wheat and Weeds at Indicated Days After Treatment | | | | | | | | |
|---|---|---|---|---|---|---|---|---|---|---|
| | | 9 | | 11 | | | 249 | | 640 | |
| Cmp. | kg./ha. | LAM | STK | PIG | WTG | RUS | RUS | WHT | WTG | RUS |
| 7 | 0.84 | 0 | 10 | 23 | 40 | 0 | 52 | 25 | 0 | 0 |
| | 1.12 | 0 | 17 | 53 | 30 | 0 | 27 | 47 | 0 | 0 |
| | 1.40 | 10 | 13 | 43 | 30 | 0 | 33 | 63 | 0 | 0 |
| | 2.80 | 20 | 13 | 47 | 33 | 0 | 72 | 97 | 97 | 90 |
| 12 | 0.84 | 0 | 7 | 13 | 27 | 0 | 30 | 58 | 0 | 0 |
| | 1.12 | 0 | 3 | 0 | 7 | 0 | 7 | 30 | 0 | 0 |
| | 1.40 | 0 | 10 | 23 | 33 | 0 | 17 | 53 | 0 | 0 |
| | 2.80 | 33 | 7 | 53 | 40 | 0 | 47 | 97 | 87 | 83 |
| Con- | | | | | | | | | | |

Table 10-continued

| | | Percent Control of Volunteer Wheat and Weeds at Indicated Days After Treatment | | | | | | | | |
|---|---|---|---|---|---|---|---|---|---|---|
| | | 9 | | 11 | | | 249 | | 640 | |
| Cmp. | kg./ha. | LAM | STK | PIG | WTG | RUS | RUS | WHT | WTG | RUS |
| trol | 0 | 0 | 0 | 0 | 0 | 0 | 0 | 0 | 0 | 0 |

FIELD TRIAL 7

This field trial was conducted in Nebraska to determine the herbicidal efficacy of the same compounds used in Field Trial 6 during a 12–13 month fallow period after the harvest of winter wheat. The compounds were applied to weeds and standing wheat stubble. The experimental design was the randomized block with 3 replicates per application rate. The plot size treated was 3.6×21.3 meters.

The test compounds were applied over the surface and were each formulated as an 80% wettable powder. On the 238th day after planting, the plots were sprayed with 2,4-dichlorophenoxyacetic acid ester at the rate of 0.56 kg./ha. Subsequently, on the 283rd day after the application of the test compounds, all plots were sprayed with a mixture of 2-chloro-N-isopropylacetanilide and isooctyl ester of 2,4-dichlorophenoxyacetic acid, at the rate of 0.56 kg./ha.

On the 393rd day after application of the test compounds, the plots were planted to winter wheat, variety Centurk, at a seeding rate of 44.8–50.4 kg./ha. at a 0.3048 meter spacing and at a depth of about 5–7.6 centimeters.

Observations were made and recorded of the effect of the test compounds on the weeds and volunteer wheat and the crop, and these observations are recorded in Table 11 which follows. Table 11 records the Percent Control of volunteer wheat and weeds at the indicated days after treatment. In Table 11A, which follows Table 11, the crop injury rating at the indicated days after treatment is recorded.

Table 11A

| Crop Injury Rating at Indicated Days After Treatment* | | |
|---|---|---|
| Cmp. | kg./ha. | 615 |
| 7 | 0.84 | 0 |
| | 1.12 | 3 |
| | 1.40 | 0 |
| | 2.80 | 3 |
| 12 | 0.84 | 0 |
| | 1.12 | 0 |
| | 1.40 | 0 |
| | 2.80 | 0 |
| Control | 0 | 0 |

*Crop Injury Rating Scale
0 = no injury
1–3 = slight injury
4–6 = moderate injury
7–9 = severe injury
10 = death

FIELD TRIAL 8

This field trial was conducted in Colorado to determine the herbicidal efficacy of the same compounds used in the above field trials during a 12–13 month fallow period after the harvest of winter wheat. The compounds were applied to weeds and standing wheat stubble. The experimental design was a randomized block with 3 replicates per rate of application. The plot size treated was 6×21.3 meters.

As in the previous field trial, the test compounds were formulated as 80% wettable powders and were applied over the surface.

On the 237th day after the test compounds were applied to the plots, a mixture of 2-chloro-N-isopropylacetanilide and isooctyl ester of 2,4-dichloro- Table 11

| | | Percent Control of Volunteer Wheat and Weeds at Indicated Days After Treatment | | | | | | | | | |
|---|---|---|---|---|---|---|---|---|---|---|---|
| | | 246 | | | | | 282 | | | | |
| Cmp. | kg./ha. | BWA | PHE | AFL | KOC | WHT | WAP | KOC | RUS | HMS | WHT |
| 7 | 0.84 | 87 | 90 | 100 | 98 | 96 | 70 | 80 | 47 | 93 | 97 |
| | 1.12 | 25 | 63 | 63 | 68 | 83 | 17 | 43 | 17 | 40 | 43 |
| | 1.40 | 90 | 81 | 99 | 72 | 60 | 67 | 77 | 37 | 73 | 70 |
| | 2.80 | 60 | 97 | 100 | 100 | 98 | 77 | 87 | 82 | 93 | 100 |
| 12 | 0.84 | 80 | 85 | 100 | 97 | 62 | 43 | 73 | 50 | 77 | 77 |
| | 0.12 | 82 | 63 | 100 | 99 | 95 | 43 | 63 | 37 | 70 | 83 |
| | 1.40 | 98 | 93 | 100 | 98 | 95 | 83 | 93 | 67 | 97 | 97 |
| | 2.80 | 77 | 100 | 100 | 100 | 90 | 100 | 100 | 100 | 100 | 100 |
| Control | 0 | 0 | 0 | 0 | 0 | 0 | 0 | 0 | 0 | 0 | 0 |

| | | 337 | | 630 | | |
|---|---|---|---|---|---|---|
| Cmp. | kg./ha. | KOC | RUS | LAM | RUS | TMS |
| 7 | 0.84 | 97 | 90 | 94 | 94 | 94 |
| | 1.12 | 80 | 83 | 91 | 93 | 89 |
| | 1.40 | 97 | 99 | 97 | 98 | 99 |
| | 2.80 | 100 | 100 | 98 | 98 | 91 |
| 12 | 0.84 | 97 | 91 | 88 | 92 | 77 |
| | 0.12 | 97 | 86 | 96 | 96 | 84 |
| | 1.40 | 100 | 90 | 91 | 94 | 79 |
| | 2.80 | 100 | 100 | 98 | 97 | 96 |
| Control | | 0 | 0 | 0 | 0 | 0 | phenoxyacetic acid was applied to the plots at a rate of 1.12 kg./ha.

Wheat, variety Centurk, was planted in the plots 387 days after treatment, the wheat being seeded at a rate of 20.2 kg./ha. at a 0.36 meter space, and to a depth of 2.54 centimeters.

Beginning in the fall after the treatments were applied and continuing in the following spring, observations were made of the percent control of volunteer wheat and weeds, and these observations are recorded in Table 12, which follows.

On the 432nd day after treatment all the plots were seeded with wheat, variety Wanser, using a deep furrow drill.

Periodic observations of the percent control of volunteer wheat and weeds and subsequently possible crop injury were made. The wheat plants were about 12.7–20.3 cm. tall at the time the crop injury ratings were made. These results are set forth in Tables 13 and 13A which follow.

Table 13

| | | Percent Control of Volunteer Wheat and Weeds at Indicated Days after Treatment | | | | | | | | | | | |
|---|---|---|---|---|---|---|---|---|---|---|---|---|---|
| | | 217 | | | 231 | | | | 255 | | | | 367 |
| Cmp. | kg./ha. | PRL | TMS | WHT | TAM | PRL | TMS | WHT | TAM | PRL | TMS | WHT | PRL | RUS |
| 7 | 0.84 | 31 | 31 | 20 | 100 | 92 | 100 | 52 | 100 | 77 | 95 | 62 | 80 | 0 |
| | 1.12 | 45 | 46 | 51 | 100 | 63 | 62 | 67 | 85 | 64 | 90 | 62 | 89 | 90 |
| | 1.40 | 77 | 79 | 80 | 100 | 87 | 99 | 75 | 100 | 87 | 100 | 82 | 89 | 95 |
| | 2.80 | 98 | 98 | 96 | 100 | 95 | 98 | 95 | 100 | 97 | 100 | 96 | 100 | 100 |
| 12 | 0.84 | 86 | 85 | 79 | 100 | 100 | 85 | 87 | 100 | 95 | 97 | 87 | 95 | 0 |
| | 1.12 | 95 | 94 | 87 | 100 | 92 | 94 | 91 | 100 | 87 | 100 | 90 | 100 | 100 |
| | 1.40 | 99 | 99 | 95 | 100 | 100 | 99 | 96 | 100 | 99 | 100 | 97 | 99 | 100 |
| | 2.80 | 100 | 100 | 99 | 100 | 100 | 100 | 99 | 100 | 100 | 100 | 99 | 100 | 100 |
| Control | | 0 | 0 | 0 | 0 | 0 | 0 | 0 | 0 | 0 | 0 | 0 | 0 | 0 |

Table 12

| | | Percent Control of Volunteer Wheat and Weeds at Indicated Days after Treatment | | | | | |
|---|---|---|---|---|---|---|---|
| | | 235 | | | | 326 | |
| Cmp. | kg./ha. | CHT | BMC | KOC | WHT | KOC | HMS |
| 7 | 0.84 | 98 | 98 | 75 | 95 | 7 | 10 |
| | 1.12 | 98 | 100 | 96 | 95 | 30 | 53 |
| | 1.40 | 98 | 100 | 79 | 94 | 37 | 47 |
| | 2.80 | 100 | 100 | 98 | 100 | 90 | 100 |
| 12 | 0.84 | 95 | 93 | 92 | 88 | 20 | 37 |
| | 1.12 | 100 | 98 | 95 | 100 | 20 | 23 |
| | 1.40 | 99 | 99 | 95 | 99 | 37 | 53 |
| | 2.80 | 100 | 100 | 98 | 100 | 97 | 100 |
| Control | | 0 | 0 | 0 | 0 | 0 | 0 |

Table 13A

| | Crop Injury Rating at Indicated Days After Treatment | |
|---|---|---|
| Cmp. | kg./ha. | 621 |
| 7 | 0.84 | 4.0 |
| | 1.12 | 2.5 |
| | 1.40 | 3.2 |
| | 2.80 | 3.2 |
| 12 | 0.84 | 3.0 |
| | 1.12 | 2.0 |
| | 1.40 | 2.7 |
| | 2.80 | 3.0 |
| Control | | 0 | 0 |

FIELD TRIAL 9

This field trial was conducted in Washington.

The same test compounds, formulated in the same manner, were applied in the same manner as in Field Trial 8. The plots in this trial measured 6.1×15.2 meters and the experimental design was the randomized block with 4 replicates per application rate. Rainfall, 0.635 centimeters, occurred 24 hours before herbicide application. By 78 days after treatment a total of 3.15 centimeters of rain had fallen. No weed population of sufficient density could be developed and rated on the test plots and controls at that time.

At 258 days after treatment, the entire plot area was sprayed with 1,1'-dimethyl-4,4'-dipyridylium dichloride at the rate of 1.1 liter of active ingredient per acre. At 301 days after treatment the standing stubble on all treatments and controls was "beat down" with a rotary cutter. At 307 days after treatment all treatments and controls of replicates 3 and 4 were disced to a depth of 5–7.6 centimeters; and at 403 days after treatment all of the plots were disced once to a depth of 5–7.6 centimeters.

FIELD TRIAL 10

This field trial, like Field Trial 9, was conducted in Washington.

The same test compounds formulated in the same manner, were applied in the same manner as in the previous field trial. The plots were the same size and the complete randomized block experimental design was followed using 2 replicates per application rate.

As in trial 9, the entire plot area was sprayed with 1,1'-dimethyl-4,4'-dipyridylium dichloride at 258 days after treatment, using the same rate of application as described in trial 9. The standing stubble on all treatments and controls was "beat down" with a rotary cutter at 301 days after treatment. The entire plot area was disced to a depth of 5–7.6 centimeters at 307 days after treatment. The entire plot area was again disced at 403 days after treatment.

Seeding the plot areas to wheat, variety Wanser, took place 432 days after treatment.

Periodic observations were made to determine the percent control of volunteer wheat and weeds and subsequently the crop injury rating of the wheat as it emerged. The wheat plants were about 12.7–20.3 cm. tall at the time the injury rating was made. These results appear in Tables 14 and 14A, which follow.

Table 14

Percent Control of Volunteer Wheat and Weeds at Indicated Days After Treatment

| Cmp. | kg./ha. | 217 | | | 231 | | | | 255 | | | 367 | |
|---|---|---|---|---|---|---|---|---|---|---|---|---|---|
| | | PRL | TMS | WHT | TAM | PRL | TMS | WHT | TAM | PRL | TMS | PRL | RUS |
| 7 | 0.84 | 32 | 32 | 20 | 100 | 92 | 99 | 55 | 100 | 77 | 94 | 97 | 100 |
| | 1.12 | 42 | 47 | 52 | 100 | 61 | 64 | 67 | 100 | 65 | 95 | 99 | 100 |
| | 1.40 | 80 | 80 | 80 | 100 | 87 | 99 | 75 | 100 | 87 | 100 | 100 | 100 |
| | 2.80 | 99 | 99 | 96 | 100 | 95 | 100 | 95 | 100 | 97 | 100 | 100 | 100 |
| 12 | 0.84 | 85 | 85 | 77 | 100 | 100 | 95 | 87 | 100 | 95 | 97 | 99 | 50 |
| | 1.12 | 95 | 95 | 87 | 100 | 92 | 100 | 91 | 100 | 87 | 100 | 100 | 100 |
| | 1.40 | 99 | 99 | 95 | 100 | 100 | 100 | 96 | 100 | 100 | 100 | 100 | 100 |
| | 2.80 | 55 | 100 | 99 | 100 | 100 | 100 | 99 | 100 | 100 | 100 | 100 | 100 |
| Control | | 0 | 0 | 0 | 0 | 0 | 0 | 0 | 0 | 0 | 0 | 0 | 0 |

Table 14A

| Cmp. | kg./ha. | Crop Injury Rating at Indicated Days After Treatment* 621 |
|---|---|---|
| 7 | 0.84 | 3.7 |
| | 1.12 | 2.7 |
| | 1.40 | 3.2 |
| | 2.80 | 2.9 |
| 12 | 0.84 | 3.3 |
| | 1.12 | 3.1 |
| | 1.40 | 2.8 |
| | 2.80 | 3.3 |
| Control | | 0 |

*Crop Injury Rating Scale
0 = no injury
1-3 = slight injury
4-6 = moderate injury
7-9 = severe injury
10 = death

FIELD TRIAL 11

This field trial was conducted in Indiana to determine the herbicidal efficacy of the same compounds used in the previous field trials during a 12-13 month fallow period after the harvest of winter wheat. The compounds were applied to wheat stubble right after the winter wheat harvest and to the existing weeds, which weeds were predominantly ragweed, morningglory, field bindweed, venice mallow, large crabgrass and green foxtail. The experimental design was a randomized block with 3 replicates per rate of application. The plot size treated was 12.2×3.05 meters.

The test compounds were applied over the surface and each test compound was formulated as a 50% wettable powder. A surfactant, 0.1% of the total volume of each application treatment, was added to each treatment.

The test results are set forth in Table 15, in which are recorded the percent control of weeds and volunteer wheat at the indicated Day After Treatment.

Table 15

Percent Control of Volunteer Wheat and Weeds at Indicated Days After Treatment

| Cmp. | kg./ha. | 40 | | | 104 | 270 | | 336 | | | | 365 | | |
|---|---|---|---|---|---|---|---|---|---|---|---|---|---|---|
| | | FOX | RAG | BRD[1] | WHT | WHT | DAN | AG[2] | RAG | VEM | DAN | AG[2] | RAG | DAN |
| 2 | 0.56 | 0 | 0 | 0 | 22 | 20 | 13 | 17 | 0 | 0 | 7 | 0 | 0 | 0 |
| | 1.12 | 7 | 10 | 0 | 17 | 23 | 17 | 10 | 0 | 0 | 0 | 20 | 42 | 0 |
| | 1.68 | 23 | 7 | 0 | 15 | 27 | 27 | 17 | 10 | 0 | 0 | 17 | 13 | 17 |
| | 2.24 | 47 | 60 | 13 | 13 | 13 | 0 | 0 | 20 | 7 | 7 | 7 | 32 | 0 |
| 3 | 0.56 | 7 | 57 | 17 | 10 | 35 | 18 | 0 | 20 | 10 | 20 | 0 | 28 | 25 |
| | 1.12 | 33 | 80 | 47 | 28 | 47 | 37 | 33 | 55 | 52 | 40 | 10 | 73 | 55 |
| | 1.68 | 47 | 82 | 33 | 32 | 37 | 30 | 52 | 92 | 83 | 63 | 7 | 87 | 28 |
| | 2.24 | 70 | 88 | 58 | 52 | 82 | 85 | 73 | 93 | 88 | 73 | 25 | 73 | 65 |
| 7 | 0.56 | 45 | 60 | 23 | 25 | 52 | 47 | 30 | 17 | 33 | 27 | 23 | 67 | 43 |
| | 1.12 | 50 | 87 | 50 | 37 | 68 | 77 | 60 | 82 | 77 | 45 | 25 | 65 | 47 |
| | 1.68 | 85 | 91 | 75 | 62 | 72 | 74 | 80 | 97 | 96 | 87 | 47 | 92 | 76 |
| | 2.24 | 95 | 98 | 88 | 83 | 92 | 94 | 81 | 97 | 97 | 93 | 67 | 95 | 90 |
| 12 | 0.56 | 23 | 10 | 0 | 23 | 17 | 17 | 13 | 13 | 13 | 37 | 7 | 40 | 30 |
| | 1.12 | 50 | 80 | 33 | 48 | 55 | 40 | 0 | 13 | 43 | 20 | 0 | 35 | 10 |
| | 1.68 | 70 | 80 | 50 | 58 | 87 | 77 | 47 | 77 | 70 | 33 | 17 | 77 | 47 |
| | 2.24 | 86 | 93 | 75 | 78 | 88 | 93 | 37 | 94 | 92 | 88 | 17 | 86 | 96 |
| 13 | 0.56 | 25 | 13 | 0 | 0 | 0 | 3 | 7 | 0 | 0 | 0 | 0 | 35 | 0 |
| | 1.12 | 47 | 53 | 20 | 20 | 13 | 17 | 0 | 30 | 20 | 23 | 0 | 40 | 30 |
| | 1.68 | 77 | 89 | 65 | 25 | 27 | 27 | 62 | 87 | 60 | 52 | 32 | 93 | 40 |
| | 2.24 | 94 | 93 | 63 | 37 | 63 | 75 | 63 | 93 | 88 | 67 | 13 | 92 | 37 |
| Control | | 0 | 0 | 0 | 0 | 0 | 0 | 0 | 0 | 0 | 0 | 0 | 0 | 0 |

[1]BRD=Broadleaves, other: plantains, dandelion, venice mallow, smartweed, velvetleaf, spurge, and cocklebur.
[2]AG=Annual Grasses: foxtails and crabgrass.

At 410 days after treatment, wheat, variety Arthur, was planted. Observations were made as to crop injury and finally as to the yield of wheat obtained from the treated plots as compared to the yield of wheat obtained from the control plots. The results are recorded in Table 15A which follows.

Table 15A

| Cmp. | kg./ha. | Crop Injury Rating at Indicated DAT | | Crop Yield % of Control |
|---|---|---|---|---|
| | | 446 | 621 | 706 |
| 2 | 0.56 | 0 | 2 | 98 |
| | 1.12 | 0 | 0 | 94 |
| | 1.68 | 0 | 3 | 95 |

Table 15A-continued

| Cmp. | kg./ha. | Crop Injury Rating at Indicated DAT 446 | 621 | Crop Yield % of Control 706 |
|---|---|---|---|---|
|  | 2.24 | 0 | 0 | 102 |
| 3 | 0.56 | 0 | 0 | 116 |
|  | 1.12 | 0 | 2 | 96 |
|  | 1.68 | 0 | 0 | 90 |
|  | 2.24 | 0 | 2 | 89 |
| 7 | 0.56 | 0 | 0 | 90 |
|  | 1.12 | 0 | 2 | 90 |
|  | 1.68 | 0 | 0 | 120 |
|  | 2.24 | 0 | 0 | 115 |
| 12 | 0.56 | 0 | 0 | 105 |
|  | 1.12 | 0 | 0 | 84 |
|  | 1.68 | 0 | 0 | 95 |
|  | 2.24 | 0 | 0 | 93 |
| 13 | 0.56 | 0 | 0 | 100 |
|  | 1.12 | 0 | 0 | 104 |
|  | 1.68 | 0 | 2 | 110 |
|  | 2.24 | 0 | 0 | 121 |
| Control | 0 | 0 | 0 | 100 |
| Tilled check | 0 | 0 | 0 | 97 |

FIELD TRIAL 12

This spring wheat fallow field trial was conducted in North Dakota.

Test compounds number 7 and number 12 were formulated as 80% wettable powders and were applied to summer fallow land in the same manner as described in the previous field trials. The plots in this trial measured 4.6×18.3 meters, and the experimental design was the randomized block with three replicates per application rate. Rainfall amounted to about 38.2 centimeters up until the time of preparing the plots for planting and planting the wheat.

At 566 days after treatment, the plots were chisel plowed and then dragged with a diamond drag. On that same day, all plots were seeded to wheat.

Because of the low moisture supply, a poor stand of new wheat was obtained, so all plots were again chisel plowed and dragged with a diamond drag at 579 days after treatment. On that same day, 579 days after treatment, the wheat was reseeded. At each seeding a disc drill was used to plant the seed at a depth of 5 centimeters.

Periodic observations were made to determine the percent control of voluntary wheat and weeds and, subsequently, the crop injury rating of the wheat as it emerged. These results appear in Tables 16 and 16A, which follow.

Table 16A

| Comp. | kg./ha. | Crop Injury Rating at Indicated Days After Treatment 663 |
|---|---|---|
| 7 | 0.84 | 0 |
|  | 1.12 | 0 |
|  | 1.40 | 0 |
|  | 2.80 | 0 |
| 12 | 0.84 | 0 |
|  | 1.12 | 0 |
|  | 1.40 | 0 |
|  | 2.80 | 0 |
| Control | 0 | 0 |

The experimental results recorded hereinbefore show that compounds coming within the scope of the generic formula (I) are useful in the novel method of killing and preventing the growth of unwanted vegetation on fallow wheatland, which method is disclosed and claimed in the instant application.

I claim:

1. A method for killing and preventing the growth of unwanted vegetation on fallow wheatland between the time of harvesting the wheat crop and the time of the next planting of winter or spring wheat which method comprises applying to the locus to be treated an herbicidally-effective amount of a compound of the formula:

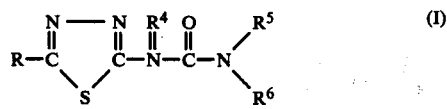

wherein
R is $R^1X$—,

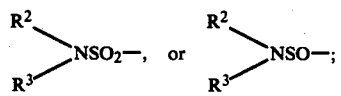

$R^1$ is lower alkyl or $C_3$–$C_7$ cycloalkyl;
X is —S—,

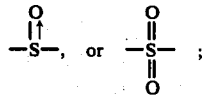

$R^2$ is hydrogen or a substituted or unsubstituted lower alkyl, the substituents being selected from the class

Table 16

| | | Percent Control of Volunteer Wheat and Weeds at Indicated Days After Treatment | | | | | | | | | | | | |
|---|---|---|---|---|---|---|---|---|---|---|---|---|---|---|
| | | 319 | | | | | | 367 | | | | 663 | | |
| Cmp. | kg./ha. | QUA | FBW | HWD | VPW | FOX | DAN | FBW | HWD | FOX | DAN | FBW | FOX | MUS | DAN |
| 7 | 0.84 | 18 | 20 | 93 | 22 | 40 | 13 | 37 | 88 | 82 | 37 | 10 | 70 | 100 | 23 |
|  | 1.12 | 12 | 20 | 94 | 68 | 38 | 20 | 30 | 100 | 53 | 32 | 30 | 83 | 100 | 35 |
|  | 1.40 | 20 | 33 | 96 | 95 | 53 | 40 | 17 | 93 | 83 | 27 | 13 | 78 | 77 | 43 |
|  | 2.80 | 74 | 66 | 98 | 72 | 95 | 76 | 40 | 100 | 95 | 42 | 50 | 99 | 100 | 78 |
| 12 | 0.84 | 10 | 17 | 95 | 33 | 30 | 10 | 67 | 80 | 85 | 0 | 17 | 75 | 78 | 20 |
|  | 1.12 | 33 | 8 | 97 | 93 | 23 | 23 | 7 | 98 | 57 | 70 | 0 | 63 | 98 | 43 |
|  | 1.40 | 68 | 8 | 98 | 95 | 23 | 23 | 17 | 100 | 82 | 70 | 20 | 66 | 90 | 20 |
|  | 2.80 | 40 | 23 | 95 | 74 | 95 | 23 | 7 | 100 | 99 | 13 | 7 | 98 | 98 | 43 |
| Control | 0 | 0 | 0 | 0 | 0 | 0 | 0 | 0 | 0 | 0 | 0 | 0 | 0 | 0 | 0 | consisting of halo, hydroxy, cyano, and lower alkoxy;

R³ is lower alkoxy, lower alkenyl, lower alkynyl, or a substituted or unsubstituted lower alkyl, the substituents being selected from the class consisting of halo, hydroxy, cyano, and lower alkoxy;

R² and R³, when taken together with the nitrogen to which they are attached, form a morpholino, piperidino, or pyrrolidino group;

R⁴ is hydrogen or lower alkyl;

R⁵ is hydrogen, lower alkyl, lower alkenyl, or C₃–C₇ cycloalkyl;

R⁶ is hydrogen, lower alkenyl, C₃–C₇ cycloalkyl, lower alkoxy, or a substituted or unsubstituted lower alkyl, the substituents being selected from the group consisting of halo, hydroxy, cyano, or lower alkoxy, except that R⁵ and R⁶ cannot both be hydrogen or a C₃–C₇ cycloalkyl; and tautomers of (I) wherein R⁴ is hydrogen; and when R⁴ is hydrogen, the alkali metal, alkaline earth metal, and ammonium salts thereof.

2. The method of claim 1 wherein the active compound is of the formula

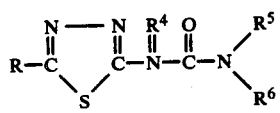 (I)

wherein

R is R¹X or

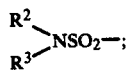

R¹ is lower alkyl or C₃–C₇ cycloalkyl;

X is —S— or

R² is hydrogen or a substituted or unsubstituted lower alkyl, the substituents being selected from the class consisting of halo, hydroxy, cyano, and lower alkoxy;

R³ is lower alkoxy, lower alkenyl, lower alkynyl, or a substituted or unsubstituted lower alkyl, the substituents being selected from the class consisting of halo, hydroxy, cyano, and lower alkoxy;

R⁴ is hydrogen or lower alkyl;

R⁵ is hydrogen, lower alkyl, lower alkenyl, or C₃–C₇ cycloalkyl;

R⁶ is hydrogen, lower alkenyl, C₃–C₇ cycloalkyl, lower alkoxy, or a substituted or unsubstituted lower alkyl, the substituents being selected from the group consisting of halo, hydroxy, cyano, or lower alkoxy, except that R⁵ and R⁶ cannot both be hydrogen or a C₃–C₇ cycloalkyl; and tautomers of (I) wherein R⁴ is hydrogen; and when R⁴ is hydrogen, the alkali metal, alkaline earth metal and ammonium salts thereof.

3. The method of claim 1 wherein the active compound is of the formula

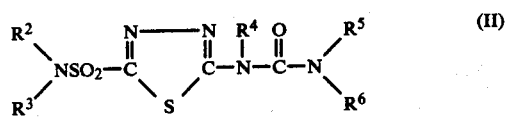 (II)

wherein

R² is unsubstituted lower alkyl;

R³ is lower alkenyl, lower alkynyl, or a substituted or unsubstituted lower alkyl, the substituents being selected from the class consisting of halo and lower alkoxy;

halo is chloro or bromo;

R⁴ is hydrogen or lower alkyl;

R⁵ is hydrogen or lower alkyl;

R⁶ is lower alkyl; and, tautomers of (II) wherein R⁴ is hydrogen; and when R⁴ is hydrogen, the alkali metal, alkaline earth metal and ammonium salts thereof.

4. The method of claim 1 wherein the active compound is 1-(5-dimethylsulfamoyl-1,3,4-thiadiazol-2-yl)-1-ethyl-3-methylurea.

5. The method of claim 1 wherein the active compound is 1-(5-dimethylsulfamoyl-1,3,4-thiadiazol-2-yl)-1,3-dimethylurea.

6. The method of claim 1 wherein the active compound is 1-[5-(N-ethyl-N-methylsulfamoyl)-1,3,4-thiadiazol-2-yl]-1,3-dimethylurea.

7. The method of claim 1 wherein the active compound is applied at the rate of from about 0.56 to about 2.2 kg./ha.

8. The method of claim 1 wherein the active compound is applied at the rate of from about 0.56 to about 1.1 kg./ha.

* * * * *

UNITED STATES PATENT AND TRADEMARK OFFICE
CERTIFICATE OF CORRECTION

PATENT NO. : 4,165,229
DATED : August 21, 1979
INVENTOR(S) : Wendell R. Arnold

It is certified that error appears in the above-identified patent and that said Letters Patent are hereby corrected as shown below:

Column 2, line 2, "plowing" should be --plowings--.

Columns 29 and 30, in Chart 2, Compound 2, at 2.2 kg./ha., under "Mustard" and "106", "00" should read --100--.

Columns 29 and 30, in Chart 2, Compound 5, at 2.2 kg./ha., under "Sorghum" and "0", "85" should read --95--.

Columns 29 and 30, in Chart 2, Compound 6, at 1.1 kg./ha., under "Mustard" and "57", "00" should read --100--.

Column 31, in Chart 3, Compound 30, at 2.2 kg./ha., under "mustard", "99" should read --100--, and the same line under "Pigweed" should read --99--.

Column 32, at line 51, "dioassays" should read --bioassays--.

Columns 33 and 34, Chart 4, Compound 31, at 1.1 kg./ha., under "Mustard" and "30", should read --5--.

UNITED STATES PATENT AND TRADEMARK OFFICE
CERTIFICATE OF CORRECTION

PATENT NO. : 4,165,229  
DATED : August 21, 1979  
INVENTOR(S) : Wendell R. Arnold Page 2 of 2

It is certified that error appears in the above-identified patent and that said Letters Patent are hereby corrected as shown below:

Columns 41 and 42, in Table 3, insert --258-- centered between "102" and "278".

Column 55, Table 14A, move "Control data and Footnotes" recorded at lines 53-57, inclusive, up and insert at lines 27-31.

Signed and Sealed this

Third Day of June 1980

[SEAL]

Attest:

SIDNEY A. DIAMOND

Attesting Officer

Commissioner of Patents and Trademarks